(12) United States Patent
Meyering et al.

(10) Patent No.: US 11,529,452 B2
(45) Date of Patent: *Dec. 20, 2022

(54) TANGENTIAL FLOW FILTER SYSTEM FOR THE FILTRATION OF MATERIALS FROM BIOLOGIC FLUIDS

(71) Applicant: MINNETRONIX, INC., St. Paul, MN (US)

(72) Inventors: Emily Rolfes Meyering, St. Louis Park, MN (US); Gary Seim, Minneapolis, MN (US); Abhi Vase, Los Altos Hills, CA (US); Ben Krehbiel, Lake City, MN (US); Blake Hedstrom, Minneapolis, MN (US); Aaron McCabe, Edina, MN (US); Jack Mondry, Edina, MN (US)

(73) Assignee: MINNETRONIX, INC., St. Paul, MN (US)

( * ) Notice: Subject to any disclaimer, the term of this patent is extended or adjusted under 35 U.S.C. 154(b) by 192 days.

This patent is subject to a terminal disclaimer.

(21) Appl. No.: 16/851,575

(22) Filed: Apr. 17, 2020

(65) Prior Publication Data

US 2020/0237979 A1 Jul. 30, 2020

Related U.S. Application Data

(62) Division of application No. 15/229,392, filed on Aug. 5, 2016, now Pat. No. 10,632,237.

(Continued)

(51) Int. Cl.
*A61M 25/00* (2006.01)
*B01D 61/14* (2006.01)
(Continued)

(52) U.S. Cl.
CPC .......... *A61M 1/884* (2021.05); *A61M 25/00* (2013.01); *B01D 61/145* (2013.01);
(Continued)

(58) Field of Classification Search
CPC .............. A61M 1/884; A61M 27/006; A61M 2202/0464; A61M 2205/3327;
(Continued)

(56) References Cited

U.S. PATENT DOCUMENTS 2,969,066 A 1/1961 Holter et al.
3,419,010 A 12/1968 Williamson
(Continued)

FOREIGN PATENT DOCUMENTS

CA 2407214 A1 4/2003
CA 2597293 A1 8/2006
(Continued)

OTHER PUBLICATIONS

US 10,532,195, 1/2020, Hedstrom et al. (withdrawn).
(Continued)

*Primary Examiner* — Joseph W Drodge
(74) *Attorney, Agent, or Firm* — Seager, Tufte & Wickhem LLP

(57) ABSTRACT

Systems and methods for filtering materials from biologic fluids are discussed. Embodiments may be used to filter cerebrospinal fluid (CSF) from a human or animal subject. In an example, CSF is separated into a permeate and retentate using a tangential flow filter. The retentate is filtered again and then returned to the subject with the permeate. During operation of the system, various parameters may be modified, such as flow rate and waste rate.

19 Claims, 10 Drawing Sheets

Related U.S. Application Data

(60) Provisional application No. 62/201,287, filed on Aug. 5, 2015.

(51) Int. Cl.
  *A61M 27/00* (2006.01)
  *B01D 61/58* (2006.01)
  *A61M 1/00* (2006.01)

(52) U.S. Cl.
  CPC ......... *B01D 61/147* (2013.01); *B01D 61/149* (2022.08); *B01D 61/58* (2013.01); *A61M 27/006* (2013.01); *A61M 2202/0464* (2013.01); *A61M 2205/3327* (2013.01); *A61M 2205/3334* (2013.01); *A61M 2205/75* (2013.01); *A61M 2230/005* (2013.01); *B01D 2313/12* (2013.01); *B01D 2313/18* (2013.01); *B01D 2315/08* (2013.01); *B01D 2315/10* (2013.01); *B01D 2317/022* (2013.01); *B01D 2317/04* (2013.01)

(58) Field of Classification Search
  CPC ...... A61M 2205/3334; A61M 2205/75; A61M 2230/005; A61M 1/88; A61M 2027/004; A61M 2206/11; A61M 5/165; A61M 2005/1652; A61M 2005/1655; A61M 2005/1657; A61M 25/002; A61M 25/00; A61M 25/043; A61M 27/00; A61M 39/0208; B01D 61/145; B01D 61/147; B01D 2313/12; B01D 2313/18; B01D 2315/08; B01D 2315/10; B01D 2317/022; B01D 2317/04; B01D 61/14; B01D 61/142; B01D 61/18; B01D 61/20; B01D 61/22; B01D 2311/06; B01D 2311/08; B01D 2311/2649; B01D 2317/02; B01D 2317/024; B01D 61/146; B01D 61/1471; B01D 61/149; B01D 61/58

See application file for complete search history.

(56) References Cited

U.S. PATENT DOCUMENTS

| | | |
|---|---|---|
| 3,867,937 A | 2/1975 | Schwartz |
| 3,889,687 A | 6/1975 | Harris et al. |
| 4,378,797 A | 4/1983 | Osterholm |
| 4,446,154 A | 5/1984 | Osterholm |
| 4,451,251 A | 5/1984 | Osterholm |
| 4,551,137 A | 11/1985 | Osborne |
| 4,686,085 A | 8/1987 | Osterholm |
| 4,695,541 A | 9/1987 | Taylor |
| 4,767,409 A | 8/1988 | Brooks |
| 4,830,849 A | 5/1989 | Osterholm |
| 4,888,115 A | 12/1989 | Marinaccio et al. |
| 4,904,237 A | 2/1990 | Janese |
| 4,950,232 A | 8/1990 | Ruzicka et al. |
| 4,958,901 A | 9/1990 | Coombs |
| 5,160,323 A | 11/1992 | Andrew |
| 5,171,226 A | 12/1992 | McCrory |
| 5,190,529 A | 3/1993 | McCrory et al. |
| 5,334,315 A | 8/1994 | Matkovitch et al. |
| 5,396,899 A | 3/1995 | Strittmatter |
| 5,405,316 A | 4/1995 | Magram |
| 5,423,738 A | 6/1995 | Robinson et al. |
| 5,456,843 A | 10/1995 | Koenhen |
| 5,462,667 A | 10/1995 | Wollinsky et al. |
| 5,531,673 A | 7/1996 | Helenowski |
| 5,560,828 A | 10/1996 | Koenhen et al. |
| 5,601,727 A | 2/1997 | Bormann et al. |
| 5,683,357 A | 11/1997 | Magram |
| 5,726,026 A | 3/1998 | Wilding et al. |
| 5,755,968 A | 5/1998 | Stone |
| 5,772,607 A | 6/1998 | Magram |
| 5,836,928 A | 11/1998 | Gerber et al. |
| 5,897,528 A | 4/1999 | Schultz |
| 5,941,853 A | 8/1999 | Collins |
| 5,947,689 A | 9/1999 | Schick |
| 5,948,441 A | 9/1999 | Lenk et al. |
| 5,980,480 A | 11/1999 | Rubenstein et al. |
| 6,013,051 A | 1/2000 | Nelson |
| 6,022,742 A | 2/2000 | Kopf |
| 6,056,725 A | 5/2000 | Elsberry |
| 6,113,797 A | 9/2000 | Al-Samadi |
| 6,217,552 B1 | 4/2001 | Barbut et al. |
| 6,238,382 B1 | 5/2001 | Schock et al. |
| 6,264,625 B1 | 7/2001 | Rubenstein et al. |
| 6,326,044 B1 | 12/2001 | Lindquist |
| 6,350,382 B1 * | 2/2002 | Schick ................. B01D 61/145 210/90 |
| 6,379,331 B2 | 4/2002 | Barbut et al. |
| 6,383,159 B1 | 5/2002 | Saul et al. |
| 6,383,380 B1 | 5/2002 | Kopf |
| 6,387,290 B1 | 5/2002 | Brody et al. |
| 6,468,219 B1 | 10/2002 | Njemanze |
| 6,537,241 B1 | 3/2003 | Odland |
| 6,558,353 B2 | 5/2003 | Zohmann |
| 6,575,928 B2 | 6/2003 | Saul et al. |
| 6,594,880 B2 | 7/2003 | Elsberry |
| 6,641,563 B1 | 11/2003 | Vitullo et al. |
| 6,682,508 B1 * | 1/2004 | Meythaler ............. A61M 25/00 604/113 |
| 6,689,085 B1 | 2/2004 | Rubenstein et al. |
| 6,689,756 B2 | 2/2004 | Hesson et al. |
| 6,699,269 B2 | 3/2004 | Khanna |
| 6,709,426 B2 | 3/2004 | Gijsbers et al. |
| 6,733,675 B2 | 5/2004 | Ando et al. |
| 6,758,832 B2 | 7/2004 | Barbut et al. |
| 6,830,561 B2 | 12/2004 | Jansen et al. |
| 6,849,185 B1 | 2/2005 | Wu et al. |
| 6,875,192 B1 | 4/2005 | Saul et al. |
| 6,969,383 B2 | 11/2005 | Hildebrand |
| 7,011,647 B2 | 3/2006 | Purdy et al. |
| 7,025,742 B2 | 4/2006 | Rubenstein et al. |
| 7,108,680 B2 | 9/2006 | Rohr et al. |
| 7,118,549 B2 | 10/2006 | Chan |
| 7,150,737 B2 | 12/2006 | Purdy et al. |
| 7,181,289 B2 | 2/2007 | Pflueger et al. |
| 7,189,221 B2 | 3/2007 | Silverberg et al. |
| 7,214,211 B2 | 5/2007 | Woehr et al. |
| 7,252,659 B2 | 8/2007 | Shehada et al. |
| 7,318,834 B2 | 1/2008 | Njemanze |
| 7,455,666 B2 | 11/2008 | Purdy |
| 7,708,716 B2 | 5/2010 | Shah |
| 7,787,954 B2 | 8/2010 | Purdy |
| 7,842,002 B2 | 11/2010 | Mantle |
| 7,850,723 B1 | 12/2010 | Magers |
| 7,887,503 B2 | 2/2011 | Geiger |
| 8,029,495 B2 | 10/2011 | Pyles |
| 8,131,353 B2 | 3/2012 | Purdy |
| 8,137,334 B2 | 3/2012 | Heruth et al. |
| 8,231,586 B2 | 7/2012 | Kizer et al. |
| 8,357,296 B2 | 1/2013 | Bonhomme et al. |
| 8,398,581 B2 | 3/2013 | Panotopoulos |
| 8,435,204 B2 | 5/2013 | Lad et al. |
| 8,444,661 B2 | 5/2013 | Nair et al. |
| 8,475,419 B2 | 7/2013 | Eckermann |
| 8,486,023 B2 | 7/2013 | Pyles |
| 8,486,104 B2 | 7/2013 | Samson et al. |
| 8,512,280 B2 | 8/2013 | Rozenberg et al. |
| 8,518,636 B2 | 8/2013 | Bosch et al. |
| 8,523,930 B2 | 9/2013 | Saunders et al. |
| 8,603,057 B2 | 12/2013 | Hoffman et al. |
| 8,669,044 B2 | 3/2014 | Chiu et al. |
| 8,679,751 B2 | 3/2014 | Huang |
| 8,721,642 B1 | 5/2014 | Sullivan |
| 8,905,968 B2 | 12/2014 | Thomas |
| 9,205,184 B2 | 12/2015 | Eckermann |
| 9,211,163 B1 | 12/2015 | Jaramaz et al. |
| 9,387,311 B1 | 7/2016 | Heilman et al. |
| 9,770,180 B2 | 9/2017 | Radojicic |
| 9,895,518 B2 | 2/2018 | Lad et al. |
| 10,272,188 B1 * | 4/2019 | Geiger ................. A61M 1/3479 |
| 10,569,064 B2 | 2/2020 | Vase et al. |

(56) References Cited

U.S. PATENT DOCUMENTS

| | | | |
|---|---|---|---|
| 10,632,237 B2 * | 4/2020 | Meyering | B01D 61/145 |
| 10,695,545 B2 * | 6/2020 | Hedstrom | A61M 27/006 |
| 10,850,235 B2 * | 12/2020 | Meyering | B01D 61/145 |
| 2002/0043487 A1 * | 4/2002 | Schick | B01D 61/145 |
| | | | 210/90 |
| 2002/0077682 A1 | 6/2002 | Lee et al. | |
| 2002/0123714 A1 | 9/2002 | Saul et al. | |
| 2002/0156482 A1 | 10/2002 | Scribner et al. | |
| 2002/0193285 A1 | 12/2002 | Hesson et al. | |
| 2002/0198579 A1 | 12/2002 | Khanna | |
| 2003/0004495 A1 | 1/2003 | Saul | |
| 2003/0014016 A1 | 1/2003 | Purdy | |
| 2003/0028137 A1 | 2/2003 | Levin | |
| 2003/0032915 A1 | 2/2003 | Saul | |
| 2003/0065309 A1 | 4/2003 | Barnitz | |
| 2003/0072761 A1 | 4/2003 | LeBowitz | |
| 2003/0083698 A1 | 5/2003 | Whitehurst et al. | |
| 2003/0097082 A1 | 5/2003 | Purdy et al. | |
| 2003/0129134 A1 | 7/2003 | Chenard et al. | |
| 2003/0130577 A1 | 7/2003 | Purdy et al. | |
| 2003/0130651 A1 | 7/2003 | Lennox | |
| 2003/0135196 A1 | 7/2003 | Hesson et al. | |
| 2003/0163181 A1 | 8/2003 | Frazer et al. | |
| 2003/0199802 A1 | 10/2003 | Barbut | |
| 2004/0015133 A1 | 1/2004 | Karim | |
| 2004/0030279 A1 | 2/2004 | Rubenstein et al. | |
| 2004/0068221 A1 | 4/2004 | Silverberg et al. | |
| 2004/0138125 A1 | 7/2004 | Wang | |
| 2004/0138728 A1 | 7/2004 | Wong et al. | |
| 2004/0142906 A1 | 7/2004 | Wang | |
| 2004/0147987 A1 | 7/2004 | Ginsburg et al. | |
| 2004/0210231 A1 | 10/2004 | Boucher et al. | |
| 2004/0215162 A1 | 10/2004 | Putz | |
| 2004/0220545 A1 | 11/2004 | Heruth et al. | |
| 2005/0004504 A1 | 1/2005 | Frye et al. | |
| 2005/0060006 A1 | 3/2005 | Pflueger et al. | |
| 2005/0090801 A1 | 4/2005 | Racz et al. | |
| 2005/0126961 A1 * | 6/2005 | Bissler | A61M 1/1647 |
| | | | 210/97 |
| 2006/0015160 A1 | 1/2006 | Larnard | |
| 2006/0016751 A1 | 1/2006 | Ali et al. | |
| 2006/0030027 A1 | 2/2006 | Ellson et al. | |
| 2006/0045796 A1 | 3/2006 | Anderle et al. | |
| 2006/0058836 A1 | 3/2006 | Bose et al. | |
| 2006/0142783 A1 | 6/2006 | Lewis et al. | |
| 2006/0175543 A1 | 8/2006 | Elefteriades | |
| 2006/0184098 A1 | 8/2006 | Barnitz et al. | |
| 2006/0224101 A1 | 10/2006 | Glenn | |
| 2006/0254984 A1 | 11/2006 | Polyakov | |
| 2006/0282043 A1 | 12/2006 | Pyles | |
| 2007/0050002 A1 | 3/2007 | Elefteriades | |
| 2007/0246406 A1 | 10/2007 | Dibel et al. | |
| 2008/0045883 A1 | 2/2008 | Radojicic | |
| 2008/0154181 A1 | 6/2008 | Khanna | |
| 2008/0171990 A1 | 7/2008 | Zauner | |
| 2008/0190848 A1 | 8/2008 | Oklejas | |
| 2008/0249458 A1 | 10/2008 | Yamasaki | |
| 2008/0249501 A1 | 10/2008 | Yamasaki | |
| 2008/0319376 A1 | 12/2008 | Wilcox et al. | |
| 2009/0000890 A1 * | 1/2009 | Furuya | B62K 21/08 |
| | | | 188/290 |
| 2009/0076357 A1 | 3/2009 | Purdy | |
| 2009/0082800 A1 | 3/2009 | Janardhan | |
| 2009/0171369 A1 | 7/2009 | Gayzik | |
| 2009/0277850 A1 | 11/2009 | Adams et al. | |
| 2010/0030196 A1 | 2/2010 | Hildebrand et al. | |
| 2010/0145267 A1 | 6/2010 | Bishop et al. | |
| 2010/0168665 A1 | 7/2010 | Skerven | |
| 2010/0179509 A1 | 7/2010 | Pyles | |
| 2010/0198195 A1 | 8/2010 | Nishtala et al. | |
| 2010/0204672 A1 | 8/2010 | Lockhart et al. | |
| 2010/0260815 A1 | 10/2010 | Kyle et al. | |
| 2010/0280438 A1 | 11/2010 | Thomas | |
| 2010/0305492 A1 * | 12/2010 | Lad | A61M 27/006 |
| | | | 604/9 |
| 2010/0324397 A1 | 12/2010 | Purdy | |
| 2011/0029050 A1 | 2/2011 | Elefteriades et al. | |
| 2011/0046547 A1 | 2/2011 | Mantle | |
| 2011/0098623 A1 | 4/2011 | Zhang et al. | |
| 2011/0190831 A1 | 8/2011 | Mafi et al. | |
| 2011/0319824 A1 | 12/2011 | Pyles | |
| 2012/0004625 A1 | 1/2012 | Velez-Rivera | |
| 2012/0149021 A1 | 6/2012 | Yung et al. | |
| 2012/0165757 A1 | 6/2012 | Purdy | |
| 2012/0203142 A1 | 8/2012 | Bedell | |
| 2012/0203290 A1 | 8/2012 | Warren et al. | |
| 2012/0209367 A1 | 8/2012 | Prindle et al. | |
| 2012/0232458 A1 | 9/2012 | Herschman | |
| 2012/0234694 A1 | 9/2012 | Vecitis et al. | |
| 2012/0253266 A1 | 10/2012 | Qureshi et al. | |
| 2012/0302938 A1 | 11/2012 | Browd et al. | |
| 2012/0330196 A1 | 12/2012 | Nita | |
| 2013/0023814 A1 | 1/2013 | Bertrand et al. | |
| 2013/0030411 A1 | 1/2013 | Kreck et al. | |
| 2013/0035628 A1 | 2/2013 | Garrison et al. | |
| 2013/0066331 A1 | 3/2013 | Chitre et al. | |
| 2013/0085413 A1 | 4/2013 | Tsamir et al. | |
| 2013/0126430 A1 * | 5/2013 | Kenley | B01D 61/00 |
| | | | 210/638 |
| 2013/0131811 A1 | 5/2013 | Barreiro et al. | |
| 2013/0158470 A1 | 6/2013 | Panotopoulos | |
| 2013/0158564 A1 | 6/2013 | Harris et al. | |
| 2013/0165903 A1 | 6/2013 | Webler et al. | |
| 2013/0197422 A1 | 8/2013 | Browd et al. | |
| 2013/0248450 A1 | 9/2013 | Kenley et al. | |
| 2014/0066830 A1 | 3/2014 | Lad et al. | |
| 2014/0166555 A1 | 6/2014 | Dibel et al. | |
| 2014/0194840 A1 | 7/2014 | Eckermann | |
| 2014/0276334 A1 | 9/2014 | Eckermann | |
| 2014/0276660 A1 | 9/2014 | Eckermann | |
| 2014/0299546 A1 | 10/2014 | Eckert et al. | |
| 2014/0316373 A1 | 10/2014 | Dhall | |
| 2014/0323857 A1 | 10/2014 | Mourad et al. | |
| 2014/0358183 A1 | 12/2014 | Saunders et al. | |
| 2015/0094644 A1 | 4/2015 | Lenihan et al. | |
| 2015/0129497 A1 * | 5/2015 | Humes | A61M 1/3489 |
| | | | 210/646 |
| 2015/0196742 A1 | 7/2015 | Browd et al. | |
| 2015/0223832 A1 | 8/2015 | Swaney et al. | |
| 2015/0224284 A1 | 8/2015 | Panotopoulos et al. | |
| 2015/0238685 A1 | 8/2015 | Elias et al. | |
| 2015/0257774 A1 | 9/2015 | Galdonik et al. | |
| 2015/0328295 A1 | 11/2015 | Lodge et al. | |
| 2016/0046503 A1 * | 2/2016 | Hoek | B01D 61/22 |
| | | | 210/741 |
| 2016/0051801 A1 | 2/2016 | Vase | |
| 2016/0101270 A1 | 4/2016 | Browd et al. | |
| 2016/0136398 A1 | 5/2016 | Heilman et al. | |
| 2016/0174995 A1 | 6/2016 | Turjman et al. | |
| 2016/0303355 A1 | 10/2016 | Heilman et al. | |
| 2016/0303356 A1 | 10/2016 | Heilman et al. | |
| 2017/0000361 A1 | 1/2017 | Meyering et al. | |
| 2017/0035950 A1 | 2/2017 | Meyering et al. | |
| 2017/0035998 A1 | 2/2017 | Meyering et al. | |
| 2017/0095649 A1 | 4/2017 | Vase et al. | |
| 2017/0157374 A1 | 6/2017 | Hedstrom et al. | |

FOREIGN PATENT DOCUMENTS

| | | |
|---|---|---|
| CA | 2793672 A1 | 9/2011 |
| CA | 2936349 A1 | 7/2015 |
| CN | 101288783 A | 10/2008 |
| CN | 101653637 A | 2/2010 |
| CN | 202409608 U | 9/2012 |
| CN | 102973305 A | 3/2013 |
| CN | 203816046 U | 9/2014 |
| CN | 203935243 U | 11/2014 |
| CN | 105361923 A | 3/2016 |
| EP | 0515007 B1 | 12/1996 |
| EP | 1331019 A2 | 7/2003 |
| EP | 2086573 A2 | 5/2011 |
| EP | 2217315 B1 | 5/2012 |
| EP | 2583744 A1 | 4/2013 |
| EP | 2695633 A1 | 2/2014 |

(56) References Cited

FOREIGN PATENT DOCUMENTS

| | | |
|---|---|---|
| EP | 2882483 B1 | 9/2016 |
| GB | 2365344 A | 2/2002 |
| JP | 03504681 A | 10/1991 |
| JP | 2001509712 A | 7/2001 |
| JP | 2001513349 A | 9/2001 |
| JP | 2002514096 A | 5/2002 |
| JP | 2003515394 A | 5/2003 |
| JP | 2003250881 A | 9/2003 |
| JP | 2003526398 A | 9/2003 |
| JP | 2004508109 A | 3/2004 |
| JP | 2004236792 A | 8/2004 |
| JP | 2004528062 A | 9/2004 |
| JP | 2006514857 A | 5/2006 |
| JP | 2006525827 A | 11/2006 |
| JP | 2010505556 A | 2/2010 |
| JP | 2010520446 A | 6/2010 |
| JP | 2011526799 A | 10/2011 |
| JP | 2018523524 A | 8/2018 |
| RU | 2100965 C1 | 1/1998 |
| RU | 2158613 C2 | 11/2000 |
| RU | 2290974 C1 | 1/2007 |
| RU | 2312678 C1 | 12/2007 |
| RU | 2314838 C2 | 1/2008 |
| WO | 8909629 A1 | 10/1989 |
| WO | 9205864 A1 | 4/1992 |
| WO | 9802202 A1 | 1/1998 |
| WO | 9833535 A1 | 8/1998 |
| WO | 9907276 A2 | 2/1999 |
| WO | 0041762 A1 | 7/2000 |
| WO | 0043056 A1 | 7/2000 |
| WO | 0051669 A1 | 9/2000 |
| WO | 0139819 A2 | 6/2001 |
| WO | 0154766 A1 | 8/2001 |
| WO | 0211703 A1 | 2/2002 |
| WO | 0220083 A2 | 3/2002 |
| WO | 0232494 A2 | 4/2002 |
| WO | 02056937 A2 | 7/2002 |
| WO | 03015710 A2 | 2/2003 |
| WO | 03020208 A2 | 3/2003 |
| WO | 03057306 A1 | 7/2003 |
| WO | 2004041314 A1 | 5/2004 |
| WO | 2004060463 A1 | 7/2004 |
| WO | 2004072647 A1 | 8/2004 |
| WO | 2004093945 A1 | 11/2004 |
| WO | 2004105839 A1 | 12/2004 |
| WO | 2005035025 A1 | 4/2005 |
| WO | 2005044335 A2 | 5/2005 |
| WO | 2005044847 A1 | 5/2005 |
| WO | 2006017763 A2 | 2/2006 |
| WO | 2006079007 A2 | 7/2006 |
| WO | 2006086195 A2 | 8/2006 |
| WO | 2007013945 A2 | 2/2007 |
| WO | 2007110643 A1 | 10/2007 |
| WO | 2008105959 A2 | 9/2008 |
| WO | 2008107652 A1 | 9/2008 |
| WO | 2009140202 A1 | 11/2009 |
| WO | 2009155384 A1 | 12/2009 |
| WO | 2009155614 A2 | 12/2009 |
| WO | 2010014447 A2 | 2/2010 |
| WO | 2010123558 A1 | 10/2010 |
| WO | 2010127071 A1 | 11/2010 |
| WO | 2010014447 A3 | 2/2011 |
| WO | 2011060317 A2 | 5/2011 |
| WO | 2011114260 A1 | 9/2011 |
| WO | 2011150323 A2 | 12/2011 |
| WO | 2012066103 A | 4/2012 |
| WO | 2012099984 A1 | 7/2012 |
| WO | 2013034602 A1 | 3/2013 |
| WO | 2013052951 A2 | 4/2013 |
| WO | 2014023551 A1 | 2/2014 |
| WO | 2014023552 A1 | 2/2014 |
| WO | 2014039780 A1 | 3/2014 |
| WO | 2014160481 A1 | 10/2014 |
| WO | 2015104631 A1 | 7/2015 |
| WO | 2015109260 A1 | 7/2015 |
| WO | 2015157320 A1 | 10/2015 |
| WO | 2016007553 A1 | 1/2016 |
| WO | 2017023419 A1 | 2/2017 |

OTHER PUBLICATIONS

"Continuous Dielectrophoretic Bacterial Separation and Concentration from Physiological Media Of High Conductivity" The Royal Society of Chemistry, Lab Chip, vol. 11, pp. 2893-2900, 2011.

Japanese Rejection of Appeal for related Japanese Patent Application No. 2009-531646, dated Jan. 25, 2016 (13 pages).

European Search Report and Opinion for European Patent Application No. 07873762.4 dated May 27, 2011 (11 pages).

International Search Report and Written Opinion of the International Searching Authority for International Patent Application No. PCT/US2016/036626, dated Sep. 8, 2016.

International Search Report and Written Opinion of the International Searching Authority for International Patent Application No. PCT/US2010/01186, dated Jun. 21, 2010 (7 pages).

International Search Report and Written Opinion of the International Searching Authority for International Patent Application No. PCT/US2007/80834, dated Oct. 28, 2008 (8 pages).

Arnold et al; "Electro-Rotation: Development of a Technique for Dielectric Measurements on Individual Cells and Particles." Journal of Electrostatics, vol. 21, pp. 151-191, 1988.

Arvin et al; "The Role of Inflammation and Cytokines in Brain Injury," Neuroscience and Biobehavorial Reviews, vol. 20, No. 3, pp. 445-452, 1996.

Banci, et al; "Metal-free superoxide dismutase forms soluble oligomers under physiological conditions: A possible general mechanism for familial ALS," PNAS, vol. 104, No. 27, pp. 11263-11267, Jul. 3, 2007.

Bayer et al; "Evaluation of the safety and immunogenicity of synthetic Aß42 (AN1792) in patients with AD," Neurology, vol. 64, pp. 94-101, Jan. 2005.

Becker et al; "Separation of Human Breast Cancer Cells from Blood by Differential Dielectric Affinity," Proc. Natl. Acad. Sci, vol. 92, pp. 860-864, Jan. 1995.

Becker et al; "The Removal of Human Leukemia Cells for Blood Using Interdigitated Microelectrodes," J. Phys. D: Appl. Phys; vol. 27, pp. 2659-2662, 1994.

Blennow et al; "Alzheimer's disease," Lancet, vol. 368, pp. 387-103, Jul. 29, 2006.

Buzzigoli et al; "Plasmapherisis treatment in Guillain-Barré syndrome: potential benefit over intravenous immunoglobin," Anaesth Intensive Care, vol. 38, No. 2, pp. 387-389, Abstract (1 page) Mar. 2010.

Cambria et al; "Clinical Experience with Epidural Cooling for Spinal Cord Protection during Thoracic and Thoracoaabdominal Aneurysim Repair," Journal of Vascular Surgery, vol. 25, No. 2, pp. 234-243, Feb. 1997.

Caughey et al, "Protofibrils, pores, fibrils and neurodegeneration: separating the responsible aggregates from the innocent bystanders," Annu. Rev. Neurosci. vol. 26, pp. 267-298, 2003.

Cook, "Combined Spinal-Epidural Techniques," Anaesthesia, vol. 55, pp. 42-64, 2000.

Covaciu et al; "Brain Temperature in Volunteers Subjected to Intranasal Cooling," Intensive Care Med; vol. 37, No. 8, Abstract (1 page) 1277-1284, Aug. 2011.

Dawson et al; "Molecular Pathways of Neurodegeneration in Parkinson's Disease," Science, vol. 302, pp. 819-822, Oct. 21, 2003.

Dekosky et al; "Looking Backward to Move Forward: Early Detection of Neurodegenerative Disorders," Science, pp. 830-834, Oct. 31, 2003.

Delhaas, "Extradural and Subarachnoid Catheterization Using the Seidinger Technique," British Journal of Anaesthesia, vol. 76, pp. 149-150, 1996.

Dias-Santagata et al; "Oxidative stress mediates tau-induced neurodegeneration in *Drosophila*", Journal of Clinical Investigation, vol. 117, pp. 236-245, Jan. 2007.

(56) References Cited

OTHER PUBLICATIONS

Dunnett et al; "Prospects for new restorative and neuroprotective treatments in Parkinson's disease", Nature, vol. 399, pp. A32-A38, SUPP, Jun. 24, 1999.
Elefteriades et al; Litigation in Nontraumatic Aortic Diseases—A Tempest in the Malpractice Maelstrom, Cardiology, vol. 109, pp. 263-272, 2008.
Enchev et al; "Historical Trends of Neuroendoscopic Surgical Techniques in the Treatment of Hydrocephalus," Neurosurgery Review, vol. 31, pp. 249-262, 2008.
Gascoyne et al; "Dielectrophoretic Separation of Cancer Cells from Blood," IEEE Transactions of Industry Applications, vol. 33, No. 3, pp. 670-678, May/Jun. 1997.
Gascoyne et al; "Isolation of Rare Cells from Cell Mixtures by Dielectrophoresis," Electrophoresis, vol. 30. No. 8, pp. 1388-1398, Apr. 2009.
Gascoyne et al; "Particle Separation by Dielectrophoresis," Electrophoresis, vol. 23, No. 13, pp. 1973-1983, Jul. 2002.
Gilman et al; "Clinical effects of Aß immunization (AN1792) in patients with AD in an interrupted trial," Neurology, vol. 64, pp. 1553-1562, May 2005.
Glabe, "Common mechanisms of amyloid oligomer pathogenesis in degenerative disease," Neurobiology of Aging, vol. 27, pp. 570-575, 2006.
Haltiwanger, S., "The Electrical Properties of Cancer Cells", www.royalrife.com/haltiwanger1, 62 pages, Jul. 2010.
Han et al; "An Electrorotation Technique for Measuring the Dielectric Properties of Cells with Simultaneous Use of Negative Quadropolar Dielectrophoresis and Electrorotation," The Royal Society of Chemistry, vol. 138, pp. 1529-1537, 2013.
Hansson et al; "Association between CSF biomarkers and incipient Alzheimer's disease in patients with mild cognitive impairment: a follow-up study," Lancet Neurol; vol. 5, pp. 228-234, Mar. 2006.
Helmy et al; "The Cytokine Response to Human Traumatic Brain Injury: Temporal Profiles and Evidence for Cerebral Parenchymal Production," Journal of Cerebral Blood Flow & Metabolism, vol. 31, pp. 658-670, 2011.
Hock et al; "Antibodies against beta-amyloid slow cognitive decline in Alzheimer's disease," Neuron, vol. 38, pp. 547-554, May 22, 2003.
Hohlfeld et al; "Autoimmune concepts of multiple sclerosis as a basis for selective immunotherapy: From pipe dreams to (therapeutic) pipelines," PNAS, vol. 101, Suppl. 2, pp. 14599-14606, Oct. 5, 2004.
Huang et al; "Electrode Design for Negative Dielectrophoresis," Measurement Science and Technolgy, vol. 2, pp. 1142-1146, Dec. 1991.
Janus et al; "A beta peptide immunization reduces behavioral impairment and plaques in a model of Alzheimer's disease," Nature, vol. 408, pp. 979-982, Dec. 2000.
Jones et al; "Multipolar Dielectrophoretic and Electrorotation Theory," Journal of Electrostatics, vol. 37, pp. 121-134, 1996.
Kessler et al; "Endothelin-1 levels in plasma and cerebrospinal fluid of patients with cerebral vasospasm after aneurysmal subarachnoid hemorrhage," Surgical Neurology, vol. 64, pp. S1:2-S1:5, 2005.
Koo et al; "Amyloid diseases: Abnormal protein aggregation in neurodegeneration," Proc. Natl. Acad. Sci; vol. 96, pp. 9989-9990, Aug. 1999.
Kuwabara et al; "Intravenous immunoglobin therapy for Guillan-Barré syndrome with IgG anti-GM1 antibody," Muscle & Nerve, pp. 53-58, Jan. 2001.
Lau et al; "Tau Protein Phosphorylation as a Therapeutic Target in Alzheimer's Disease," Current Topics in Medicinal Chemistry, vol. 2, pp. 395-415, 2002.
Levi et al; "Clinical Application of Modest Hypothermia After Spinal Cord Injury," J. Neurotrauma, vol. 26, No. 3, Abstract (1 page) pp. 407-415, Mar. 2009.
Li et al; "Continuous Dielectrophoretic Cell Separation Microfluidic Device," The Royal Society of Chemistry, Lab Chip, vol. 7, pp. 239-248, 2007.

Macdonald et al; "Cerebral vasospasm after subarachnoid hemorrage: the emerging revolution," Nature Clinical Practice, Neurology, vol. 3, No. 5, pp. 256-263, May 2007.
Madeira-Lopes et al; Comparative Study of the Temperature Profiles of Growth and Death of the Pathogenic feast Cryptococcus Neoformans and the non-pathogenic Cryptococcus Albidus, Journal of Basic Microbiology, vol. 26, pp. 43-47, 1986.
Markx et al; "Dielectrophoretic Separation of Bacteria Using a Conductivity Gradient," Journal of Biotechnology, vol. 51, pp. 175-180, Dec. 1996.
Markx et al; "Dielectrophoretic Separation of Cells: Continuous Separation," Biotechnology and Bioengineering, vol. 45, No. 4, pp. 337-343, Feb. 1995.
Marszalek et al; "Determination of Electrical Parameters of Cell Membranes by a Dielectrophoresis Method," Biophysical Journal, vol. 59, pp. 982-987, May 1991.
Written Opinion of the International Searching Authority for International Patent Application No. PCT/US2016/064721, dated Feb. 17, 2017 (7 pages).
Written Opinion of the International Searching Authority for International Patent Application No. PCT/US2016/55724, dated Feb. 15, 2017 (11 pages).
Firer, "Efficient elution of functional proteins in affinity chromatography," J. Biochem. Biophys. Methods 49, pp. 433-442, 2001.
Extended EP Search Report dated Mar. 4, 2019 for EP application No. 16833454.8, 7 pages.
Dias, et al., "The hydrophobic effect and its role in cold denaturation", Cryobiology, 60: 91-99, 2010.
Chevrefils, et al., "UV Dose Required to Achieve Incremental Log Inactivation of Bacteria, Protozoa and Viruses", IUVA News, 8(1): 38-45, Mar. 2006.
Prates, et al., "Photodynamic therapy can kill Cryptococcus neoformans in in vitro and in vivo models", Proc. of SPIE, vol. 7165, 2009.
Pitera, et al., "Dielectric Properties of Proteins from Simulation: The Effects of Solvent, Ligands, pH, and Temperature", Biophysical Journal, 80(6): 2546-2555, Jun. 2001.
Han, et al., "Lateral-Driven Continuous Dielectrophoretic Microseparators for Blood Cells Suspended in a Highly Conductive Medium", Lab on a Chip, 8(7):1079-1086, Jun. 27, 2008.
Baumann, et al., "The Electrical Conductivity of Human Cerebrospinal Fluid at Body Temperature", IEEE Transactions on Biomedical Engineering, 44(3): 220-223, Mar. 1997.
Park, et al., "3-D Electrode Designs for Flow-through Dielectrophoretic Systems", Electrophoresis, 26(19): 3745-3757, Oct. 2005.
Chen, et al., "A 3D Paired Microelectrode Array for Accumulation and Separation of Microparticles", J. of Micromechanics and Microengineering, 16(7): 1162-1169, Apr. 28, 2006.
Mascia et al; "Temporal Relationship Between Endothelin-1 Concentrations and Cerebral Vasospasm in Patients With Aneurysmal Subarachnoid Hemorrhage—Editorial Comment: Endothelin-1 in Vasospasm After SAH," Stroke, pp. 1185-1190, May 2001.
Mcculloch et al; "A radical approach to stroke therapy," PNAS, vol. 98, No. 20, pp. 10989-10991, Sep. 25, 2001.
Mckeating et al; "Cytokines and Adhesion Molecules in Acute Brain Injury," British Journal of Anaesthesia, vol. 80, pp. 77-84, 1998.
Mckhann et al; "Plasmapherisis and Guillain-Barré syndrome: analysis of prognostic factors and the effect of plasmapheresis," Annals of Neurology, vol. 23, No. 4, pp. 347-353, Apr. 1988.
Melnikova, "Therapies for Alzheimer's disease," Nature Reviews, vol. 6, pp. 341-342, May 2007.
Misaki et al; "Contrast-Enhanced Fluid-Attenuated Inversion Recovery MRI is useful to Detect the CSF Disseminatior of Glioblastoma," Journal of Computer Assisted Tomography, vol. 25, No. 6, pp. 953-956, 2001.
Monsonego et al; "Immunotherapeutic Approaches to Alzheimer's Disease", Science, vol. 302,pp. 834-838, Oct. 31, 2003.
Morgan et al; "A beta peptide vaccination prevents memory loss in an animal model of Alzheimer's disease," Nature, vol. 408, pp. 982-985, Dec. 2000.
Morganti-Kossman et al; "Production of Cytokines Following Brain Injury: Beneficial and Deleterious for the Damaged Tissue," Molecular Psychiatry, vol. 2, pp. 133-136, 1997.

(56) References Cited

OTHER PUBLICATIONS

Niicoll et al; "Abeta species removal after abeta42 immunization," Journal of Neuropathology Exp. Neurol; vol. 65, No. 11, pp. 1040-1048, Nov. 2006.

Noseworthy, "Progress in determining the causes and treatment of multiple sclerosis," Nature, vol. 399, Supp., pp. A40-A47, Jun. 24, 1999.

Onda et al; "Cerebral Glioblastoma with Cerebrospinal Fluid Dissemination: A Clinicopathological Study of 14 Cases Examined by Complete Autopsy," Neurosurgery, vol. 25, No. 4, pp. 533-540, 1989.

Orogozo et al; "Subacute meningoencephalitis in a subset of patients with AD after Aß42 immunization," Neurology, vol. 61, pp. 46-54, Jul. 2003.

Park et al; "3-D Electrode Designs for Flow-Through Dielectrophoretic Systems," Electrophoresis, vol. 26, pp. 3745-3757, 2005.

Parkhill et al; "The genome sequence of the food-borne pathogen Campylobacter jejuni reveals hypervariable sequences," Nature, vol. 403, pp. 665-668, Feb. 10, 2000.

Perfect, "Cryptococcus Neoformans: The Yeast that Likes it Hot," FEMS Yeast Res; vol. 6, pp. 463-468, 2006.

Pethig et al; "Applicants of Dielectrophoresis in Biotechnology," Tibtech, vol. 15, pp. 426-432, Oct. 1997.

Pethig, "Dielectrophoresis: Status of the Theory, Technology, and Applications," Biomicrofluidics, vol. 4, pp. 022811-1-02281-35, 2010.

Pethig, "Dielectrophoresis: Using Inhomogeneous AC Electrical Fields to Separate and Manipulate Cells," Critical Reviews in Biotechnology, vol. 16, No. 4, pp. 331-348, 1996.

Polderman et al; "Therapeutic Hypothermia and Controlled Normothermia in the Intensive Care Unit: Practical Considerations, Side Effects, and Cooling Methods," Crit. Care Med; vol. 37, No. 3, Abstract (1 page), Mar. 2009.

Reiber, "Proteins in cerebrospinal fluid and blood: Barriers, CSF flow rate and source-related dynamics", Restorative Neurology and Neuroscience, vol. 21, pp. 79-96, 2003.

Roberson et al; "100 Years and Counting: Prospects for Defeating Alzheimer's Disease," Science, vol. 314, pp. 781-784, Nov. 3, 2006.

Rowland, "Amyotrophic Lateral Sclerosis: Human Challenge for Neuroscience," Proc. Natl. Acad. Sci; vol. 92, pp. 1251-1253, Feb. 1995.

Shoulson, "Experimental Therapeutics of Neurodegenerative Disorders: Unmet Needs," Science, vol. 282, pp. 1072-1074, Nov. 6, 1998.

Steece-Collier et al; "Etiology of Parkinson's disease: Genetics and environment revisited," PNAS, vol. 99, No. 22, pp. 13972-13974, Oct. 29, 2002.

Stephens et al; "The Dielectrophoresis Enrichment of CD34 Cells from Peripheral Blood Stem Cell Harvests," vol. 18, pp. 777-782, 1996.

Tay et al; "Electrical and Thermal Characterization of a Dielectrophoretic Chip with 3D Electrodes for Cells Manipulation," Electrochimica. Acta; vol. 52, pp. 2862-2868, 2007.

Taylor et al; "Toxic Proteins in Neurodegenerative Disease," Science, vol. 296, pp. 1991-1995, Jun. 14, 2002.

Author Unknown, "External CSF Drainage," Aqueduct Neurosciences, (2 pages), Jul. 2014.

Author Unknown, "Therapeutic Hypothermia for Spinal Cord Injury," Crit. Care Med. vol. 37, Supp. 7, Abstract (1 page), Jul. 2009.

Author Unknown, "LiquoGuard", Moller Medical, Brochure, 2 pages, published on or before 2015.

Author Unknown, World Journal of Radiology, vol. 4, No. 6, pp. 241-290, Jun. 28, 2012.

Valentine et al; "Misfolded CuZnSOD and amyotrophic lateral sclerosis," PNAS, vol. 100, No. 7, pp. 3617-3622, Apr. 1, 2003.

Vernino et al; "Autoimmune encephalopathies," The Neurologist, vol. 13, No. 3, May 2007.

Voldman, "Electrical Forces for Microscale Cell Manipulation," Annu. Rev. Biomed. Eng; vol. 8, pp. 425-454, 2006.

Weis et al; "Noninvasive Monitoring of Brain Temperature During Mild Hypothermia," vol. 27, No. 7, Abstract (1 page ), Sep. 2009.

Wollinsky et al; CSF filtration is an effective treatment of Guillan-Barré syndrome: A randomized clinical trial, Neurology, vol. 57, pp. 774-780, Sep. 2001.

Yuki et al; "Carbohydrate mimicry between human ganglioside GM1 and Campylobacter Jejuni lipooligosaccaride causes Guillain-Barré syndrome," PNAS, vol. 101, No. 31, pp. 11404-11409, Aug. 3, 2004.

Ziebell et al; Involvement of Pro- and Anti-Inflammatory Cytkines and Chemokines in the Pathophysiology of Traumatic Brain Injury, Neurotherapeutics: The Journal of the American Society for Experimental NeuroTherapeutics, vol. 7, pp. 22-30, Jan. 2010.

European Office Action for European Patent Application No. 07873762.4, dated Dec. 7, 2016 (5 pages).

Mahon et al; North American Clinical Experience with the EKOS MicroLysUS Infusion Catheter for the Treatment of Embolic Stroke, AJNR Am J. Neuroradiology, vol. 24, pp. 534-538, Mar. 2003.

Rogers et al; "Percutaneous aspiration of brain tumor cysts via the Ommaya reservoir system," Neurology, vol. 41, pp. 279-282, Feb. 1991.

Siddiqui et al; "Use of the Penumbra System 054 plus Low Dose Thrombolytic Infusion for Multifocal Venous Sinus Thrombosis," Interventional Neuroradilogy, vol. 18, pp. 314-319, 2012.

Spiegelberg GmbH & Co. KG, "EVD-Catheters," downloaded on Nov. 3, 2016 from website, http://www.spiegelberg.de/products/drainage/silverline_evd_catheter_3001002.html (1 page).

Wagner et al; "Ultra-early clot aspiration after lysis with tissue plasminogen activator in a porcine model of intracerebral hemororrhage: edema reduction and blood-brain barrier protection," J. Neurosurg; vol. 90, pp. 491-498, Mar. 1999.

Ziu et al; "A Series of Cerebral Venous Sinus Thromboses Treated with Intra-Arterial tPA infused over Ten Hours with a 0.027-inch Catheter and Literature Review," pp. 1-13, Jun. 23, 2016.

International Search Report for International Patent Application No. PCT/US2016/55724, dated Feb. 15, 2017 (7 pages).

International Search Report for International Patent Application No. PCT/US2016/064721, dated Feb. 17, 2017 (3 pages).

\* cited by examiner

TANGENTIAL FLOW FILTER SYSTEM FOR THE FILTRATION OF MATERIALS FROM BIOLOGIC FLUIDS

CROSS-REFERENCE TO RELATED APPLICATIONS

This application is a divisional of U.S. application Ser. No. 15/229,392, filed Aug. 5, 2016, now U.S. Pat. No. 10,632,237, which claims the benefit of priority under 35 U.S.C. § 119 of U.S. Provisional Application Ser. No. 62/201,287, filed Aug. 5, 2015, which is hereby incorporated by reference in their entirety.

Embodiments described in this application may be used in combination or conjunction, or otherwise, with the subject matter described in one or more of the following:

U.S. patent application Ser. No. 15/177,638, filed Jun. 9, 2016, entitled "Tangential Flow Filter System for the Filtration of Materials from Biologic Fluids," which claims priority to U.S. Provisional Application No. 62/201,287, filed Aug. 5, 2015;

U.S. patent application Ser. No. 14/743,652, filed Jun. 18, 2015, entitled "Devices and Systems for Access and Navigation of Cerebrospinal Fluid Space," which claims priority to U.S. Provisional Application No. 62/038,998, filed Aug. 19, 2014; and U.S. patent application Ser. No. 13/801,215, filed Mar. 13, 2013, entitled "Cerebrospinal Fluid Purification System," a continuation of U.S. patent application Ser. No. 12/444,581, filed Jul. 1, 2010, which issued as U.S. Pat. No. 8,435,204 and is the U.S. National Phase entry of International Patent Application Number PCT/US2007/080834, filed Oct. 9, 2007, which claims the benefit of U.S. Provisional Application No. 60/828,745, filed on Oct. 9, 2006.

Each and every one of these documents is hereby incorporated by reference as if fully set forth herein.

BACKGROUND

A variety of diseases and conditions may be treated by filtering particular materials from biologic fluids. The most common filters for removing materials from biologic fluids are dead-end (common syringe filters), depth filters and affinity filters. Although dead-end and depth filters are easy to use and come in many pore sizes, their small surface area prevents them from being used for larger volumes or when trying to remove a significant amount of material. These filters may quickly clog because the mechanism of filtration deposits the material on the surface of the filter. In addition, the filtration of biologic materials, such as blood, may cause the material to be lysed when filtered through dead-end filters. There exists a need in the art for improved systems and methods for filtering biologic fluids.

SUMMARY

Technologies are generally described that include methods and systems.

An example method may be for filtering materials from cerebrospinal fluid (CSF) of a human or animal subject. An example method may include withdrawing a volume of fluid comprising CSF from a CSF-containing space of a subject using a filtration system. An example method may include filtering the volume of fluid into permeate and retentate using a first filter of the filtration system, wherein the first filter comprises a tangential flow filter. An example method may include returning the permeate to the CSF-containing space of the subject. An example method may include filtering the retentate using a second filter of the filtration system. An example method may include returning the filtered retentate to the CSF-containing space of the subject.

In some examples, the second filter of the filtration system includes a dead end filter or a depth filter. In some examples, the method further includes prior to returning the permeate and prior to returning the filtered retentate, combining the permeate and the filtered retentate at a combiner; and returning the combined permeate and the filtered retentate to the CSF-containing space of the subject, thereby returning the permeate and returning the filtered retentate. In some examples, the combiner includes a check-valve configured to resist back flow into the second filter. In some examples, the method further includes calculating a waste rate of the filtration system and modifying one or more parameters of the system to maintain a waste rate of less than a threshold. In some examples, the threshold is based on a predicted rate of natural CSF production in the subject. In some examples, the threshold is 0.25 milliliters of CSF per minute. In some examples, the threshold is 0.20 milliliters of CSF per minute. In some examples, the second filter of the filtration system includes a tangential flow filter configured to filter the retentate into a second permeate and a second retentate, and returning the filtered retentate to the CSF-containing space of the subject includes returning the second permeate to the CSF-containing space of the subject. In some examples, the method further includes filtering the second retentate using a third filter of the filtration system; and returning the filtered second retentate to the CSF-containing space of the subject.

In another example, a method includes withdrawing a volume of fluid comprising CSF from a CSF-containing space of a subject using a filtration system. An example method may include filtering the volume of fluid into permeate and retentate using a first filter of the filtration system, wherein the first filter comprises a tangential flow filter. An example method may include filtering the retentate using a plurality of second filters of the filtration system operating in parallel. An example method may include combining the permeate and the filtered retentate at a combiner. An example method may include returning the combined permeate and the filtered retentate to the CSF-containing space of the subject. In an example method, the plurality of second filters include one or more dead end filters or depth filters. In an example method, the combiner includes a check-valve configured to prevent back flow into the plurality of second filters. An example method may include calculating a waste rate of the system and modifying one or more parameters of the system to maintain a waste rate of less than a threshold. In an example, the threshold is 0.20 milliliters of CSF per minute.

In another example, a system for filtering materials from cerebrospinal fluid (CSF) of a human or animal subject, may include a first filter comprising a tangential flow filter configured to filter a volume of CSF into permeate and retentate, the first filter having a permeate outlet for the permeate and a retentate outlet for the retentate. An example system may include a second filter having an intake and an outlet, the intake coupled to the retentate outlet. An example system may include a combiner having an intake coupled to the permeate outlet and the outlet of the second filter. The combiner may be configured to combine the fluid filtered by the second filter and the retentate, wherein the combiner has an outlet for returning fluid to a CSF-containing space of the subject.

In some examples, the second filter comprises a dead end or depth filter. In some examples, the combiner includes a check-valve configured to prevent back flow into the second filter. In some examples, the second filter includes a tangential flow filter configured to filter the retentate into a second permeate and a second retentate, the second filter having a second permeate outlet for the second permeate and a second retentate outlet for the second retentate. In some examples, the system further include a third filter having an intake coupled to the second retentate outlet; and the combiner is coupled to the permeate outlet, the second permeate outlet, and an outlet of the third filter, and configured to combine the retentate, the second retentate of the second filter, and the fluid filtered by the third filter. In some examples, the second filter comprises a plurality of dead end or depth filters arranged in parallel. In some examples, the plurality of dead end filters or depth filters in parallel are self-regulating, such that as one of the dead end filters or depth filters becomes full, or clogged, pressure increases, resulting in more waste fluid being directed to one or more other dead end filters or depth filters.

DETAILED DESCRIPTION

Disclosed embodiments generally relate to systems and methods for filtering materials from biologic fluids of a human or animal subject. In certain implementations, a tangential flow filter may be used to separate cerebrospinal fluid (CSF) into permeate and retentate. The permeate may be returned to the subject. In certain implementations, the retentate may be filtered again, for example, through one or more additional tangential flow filters or through different methods of filtering. During operation of the system, various parameters may be modified, such as flow rate and pressure. Certain systems and methods described herein may be combined with other systems and methods for conditioning, removing, or otherwise processing biological materials, such as those discussed in U.S. Pat. No. 8,435,204, previously incorporated by reference.

Figure 1:
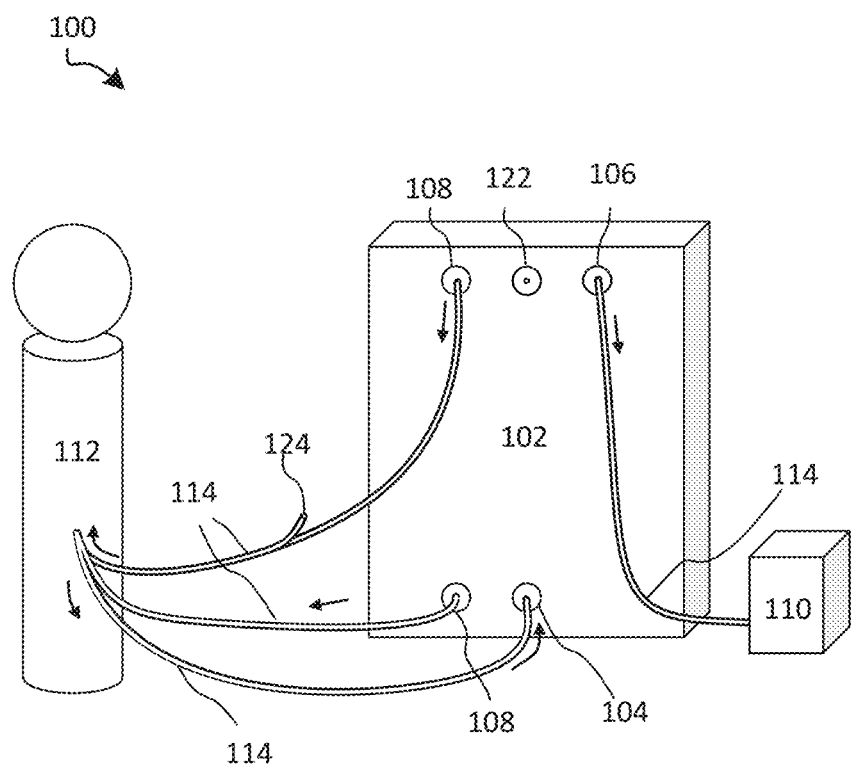
FIG. 1 illustrates a system for the filtration of materials from biologic fluids according to certain implementations, with solid arrows indicating an example fluid flow direction.

FIG. 1 illustrates a system 100 for the filtration of materials from biologic fluids according to certain embodiments, including a filtration system 102, an intake 104, a retentate outlet 106, a permeate outlet 108, a vessel 110, a reservoir 112, and tubing 114. The arrows represent an example direction that fluid may take through the system.

In certain embodiments, the filtration system 102 is a device or combination of devices that is configured to filter, concentrate, dialyze, separate, or otherwise treat or condition the contents of a fluid. The filtration system 102 may be a tangential flow filtration system (for example, as shown and described in relation to FIG. 2) or other system configured to filter fluid. In certain embodiments, the filtration system 102 receives the fluid through the intake 104 and separates the fluid into retentate and permeate. The retentate exits the filtration system 102 through a retentate outlet 106, and the permeate exits the filtration system 102 through a permeate outlet 108.

The intake 104 may be a port through which fluid enters the filtration system 102. The retentate outlet 106 may be an outlet through which retentate exits the filtration system 102. The permeate outlet 108 may be an outlet through which permeate exists the filtration system 102.

The intake 104, retentate outlet 106, and permeate outlet 108 may be any kind of ports through which material or fluid may flow. These components may be configured to be in fluid connection by tubing 114. The components 104, 106, 108, 114 may include various fittings to facilitate the connection, including but not limited to compression fittings, flare fittings, bite fittings, quick connection fittings, Luer-type fittings, threaded fittings, and other components configured to enable fluid or other connection between two or more components. In addition to fittings, the components 104, 106, 108, 114 may also include various elements to facilitate use of the system 100, including but not limited to various valves, flow regulators, adapters, converters, stopcocks, reducers, and other elements.

In certain embodiments, there may be one or more permeate outlets 108 and one or more retentate outlets 106. For example, the systems 100, 300 illustrated in FIGS. 1 and 3, respectively, include a filtration system 102 having two permeate outlets 108. This configuration may facilitate the use of different filtration systems within a filtration system 102, 302. For example, the filtration systems 102, 302 may include multiple filtration components, each with their own individual outlets.

The vessel 110 may be a container for storing fluid. For example, fluid leaving the filtration system 102 may be deposited in the vessel 110. The fluid deposited in the vessel 110 may be held for storage, waste disposal, processing, testing, or other uses. The vessel 110 may also be a reservoir for subsequent filtering, for example, through the same or different set of filters. This fluid may or not be combined with previously filtered fluid.

The reservoir 112 may contain a particular fluid to be filtered. In certain implementations, the reservoir 112 may be an anatomical entity or location within a human or animal subject, such as a chamber or CSF-containing space or a blood vessel. The reservoir 112 may be the source of the fluid, the destination of the fluid, or both. For example, the system 100 may remove or receive a volume of fluid from the reservoir 112, perform filtration and/or other treatment, and return a portion of the processed and/or treated fluid to the reservoir 112.

The various components of the system 100 may be connected through tubing 114. For instance, in certain embodiments, there may be a length of the tubing 114 placing the reservoir 112 in fluid connection with the intake 104. The permeate outlet 108 may be in fluid connection with the reservoir 112 via a length of the tubing 114. The retentate outlet 106 may be in fluid connection with the vessel 110 via a length of the tubing 114. The tubing 114 may be any kind of system for transporting or containing fluid. While the connections within the system 100 are shown as being direct, the connections need not be. The various portions of the system 100 may be connected through combinations of connections and various tubing 114. In certain embodiments, the tubing 114 and other portions of the system 100 may be filled with priming fluid (e.g., saline). Longer lengths of tubing 114 may correspondingly comprise a larger amount of priming fluid; however, in certain implementations, larger amounts of priming fluid may result in an undesirable amount of dilution of "natural" fluid, such as CSF. Accordingly, in certain implementations, the tubing 114 may be selected in order to minimize the volume of priming fluid needed, while still having the system be practically useful (e.g., enough tubing to enable the system 100 to be used at a subject's bedside). Depending on the subject and the reservoir 112, the tolerance for removal or dilution of fluid may vary, and the system 100 may be scaled accordingly. For example, the parameters of the system 100 may be changed to scale to suit subjects ranging from a mouse to a human or larger mammal.

In certain implementations, the tubing 114 may have a port 124 to access the fluid traveling within the tubing 114. As illustrated in FIG. 1, there is a port 124 between the permeate outlet 108 and the reservoir 112. This port 124 may be configured for the introduction of additives, such as therapeutic agents, artificial fluid (such as artificial CSF), and/or other additives. The port 124 may also be configured for the removal of fluid for testing or other purposes. For example, in certain embodiments, fluid returning to the reservoir 112 may be removed and tested for particular characteristics or parameters. In certain embodiments, tubing 114 that links the reservoir 112 to the intake 104 may include a port 124. This port 124 may also be used for the introduction of additives and/or the removal of fluid. In certain implementations, instead of or in addition to a port 124 located on the tubing 114, there may also be a port 122 located on the filtration system 102 itself. This port 122 may be used to access the fluid within the filtration system 102 at various points during filtration for various purposes. For example, like the port 124, the port 122 may be used to introduce additives to the system 100 or remove fluid therefrom. In some embodiments, the ports 122, 124 may be used to link the system 100 with other systems.

Figure 2A:
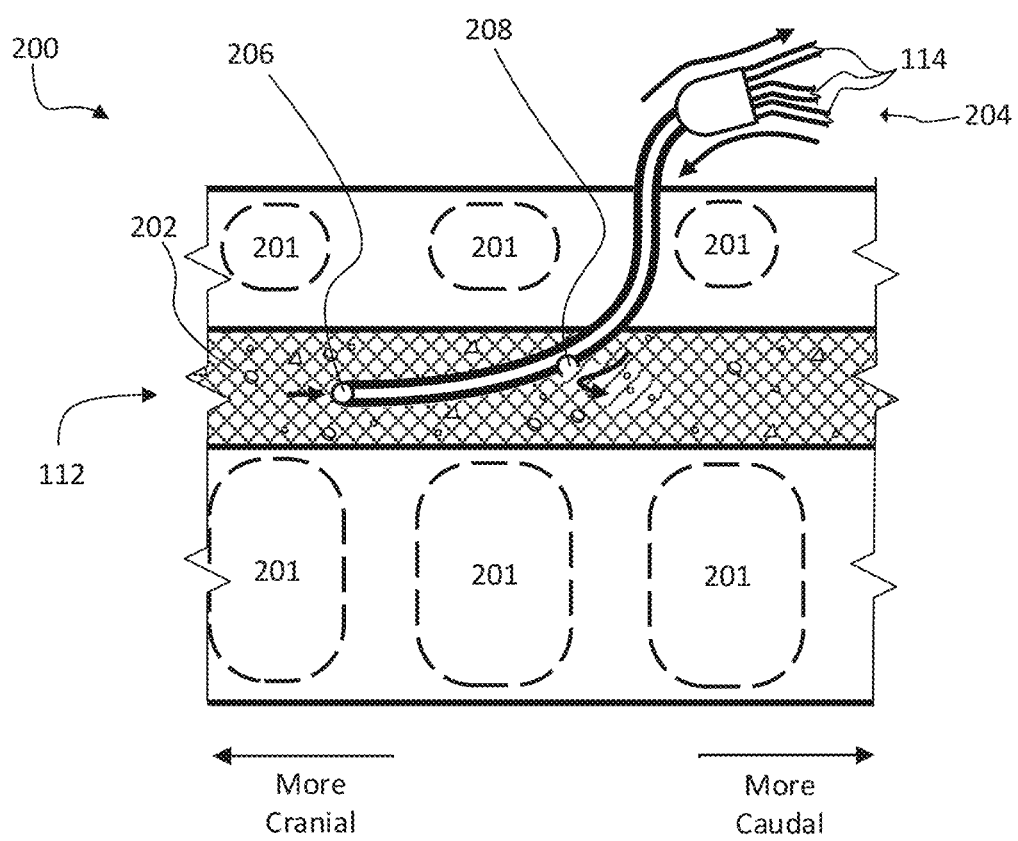
FIG. 2A illustrates fluid being withdrawn from and returned to a reservoir, according to certain implementations

FIG. 2A illustrates a system and method for withdrawing a fluid 202 from and returning fluid to the reservoir 112, according to certain implementations. The connection between the system 100 and anatomical structures (such as the reservoir 112) may be made in a variety of ways. For example, if the reservoir 112 is an anatomical location within a subject, as shown in FIG. 2A, the connection with the reservoir 112 may be made through one or more catheters inserted into particular anatomical locations. For example, the catheter may be a multi-lumen catheter inserted through a single opening in the subject to access the anatomical location or may be two catheters inserted at two different, but connected anatomical locations. In certain implementations, the connection may be made via an external ventricular drain system. For example, the tip of a catheter may be placed in a lateral ventricle of the brain.

As a specific example, the certain implementations shown in FIG. 2A include a portion of a subject's spine 200, including vertebrae 201, carrying a fluid 202 (for example, a fluid comprising CSF), and a multi-lumen catheter 204. The multi-lumen catheter 204 may comprise a first port 206 and a second port 208 that place the reservoir 112 in fluid connection with tubing 114. As illustrated, a first volume of the fluid 202 enters the multi-lumen catheter 204 through the first port 206 and is passed through into a portion of the tubing 114 (for example, a portion of tubing 114 leading to the intake 104). A second volume of fluid 202 enters the multi-lumen catheter 204 from a portion of the tubing 114 (for example, a portion of tubing 114 coming from the permeate outlet 108) and exits the multi-lumen catheter 204 through the second port 208.

Figure 2B:
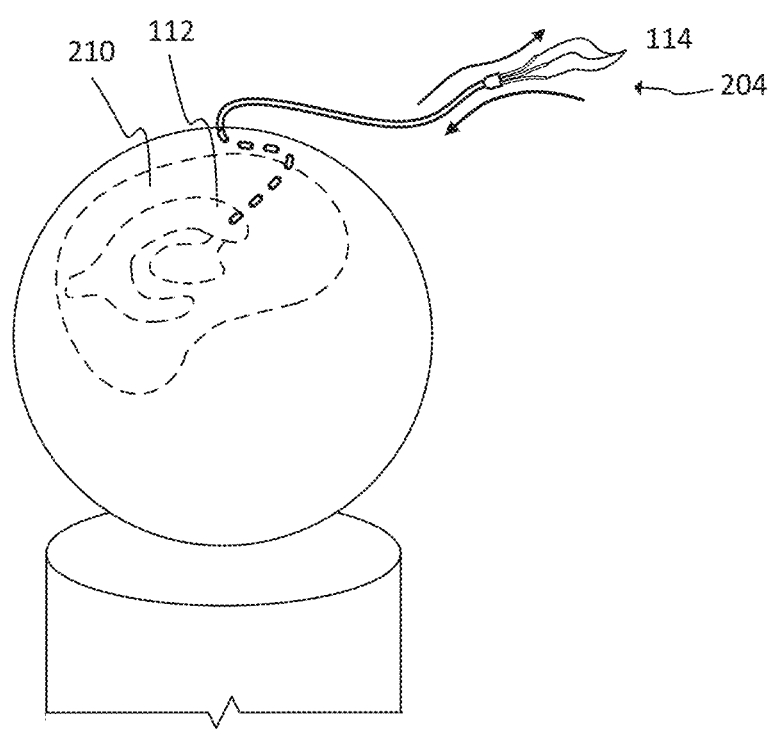
FIG. 2B illustrates fluid being withdrawn from and returned to a reservoir, according to certain implementations.

FIG. 2B illustrates a system and method for withdrawing fluid from and returning fluid to the reservoir 112, according to certain implementations. In this particular example, the multi-lumen catheter 204 is placed in fluid connection with the ventricles of a subject's brain 210 in a configuration typically referred to as an external ventricular drain.

Although FIGS. 2A and 2B illustrate accessing CSF in a portion of the spine 200 and a portion of the brain 210, respectively, the embodiments disclosed herein need not be limited to those regions or that fluid and may be used with other locations and fluids. For example, one or more single-lumen catheters may be used to transport the fluid 202. As another example, the anatomical location may be a blood vessel and the fluid may be blood.

Figure 2C:
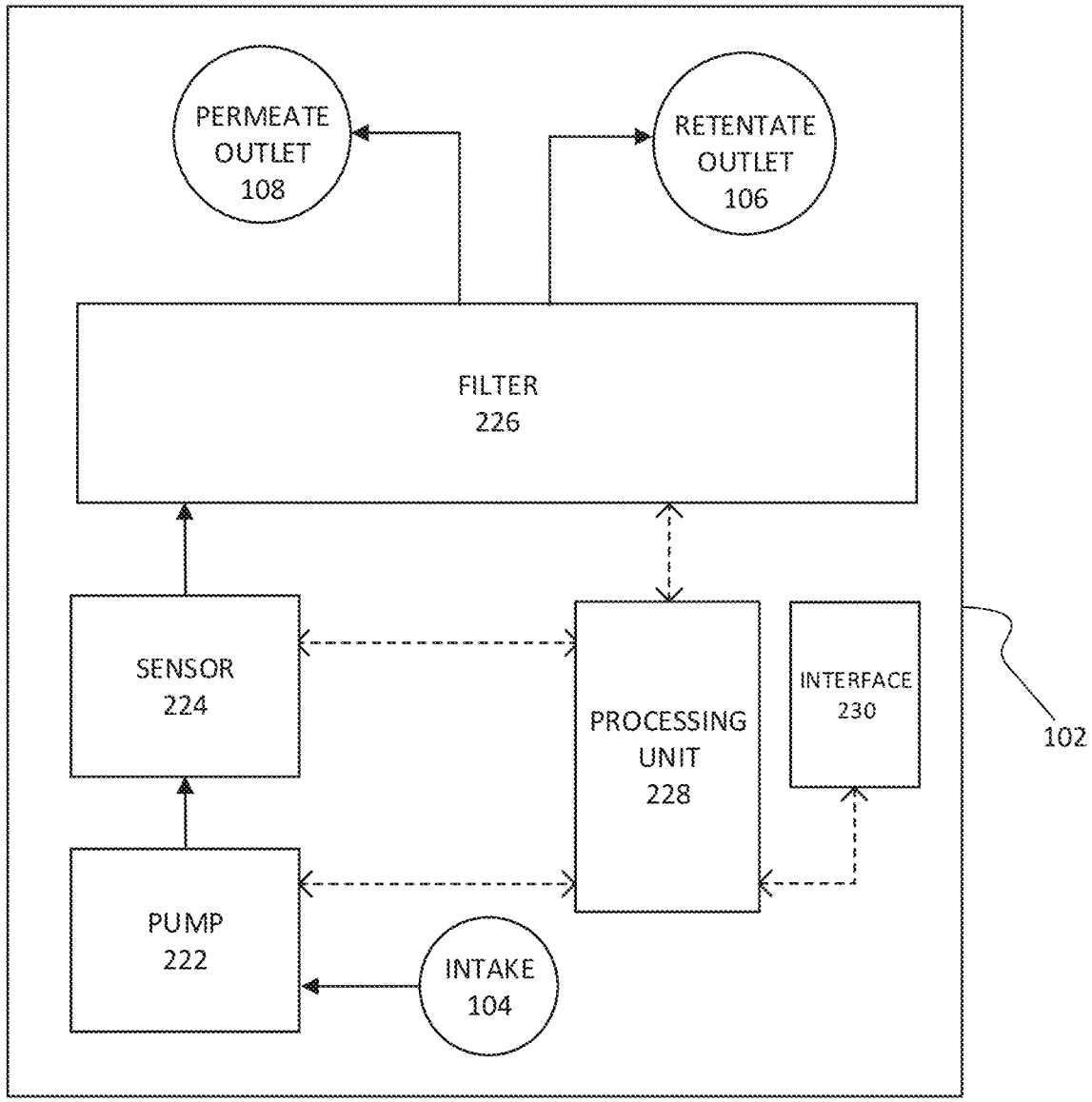
FIG. 2C illustrates a block diagram of a filtration system, according to certain implementations, with solid arrows indicating an example fluid flow path and dashed arrows indicating an example flow path for signals or information.

FIG. 2C illustrates a block diagram of a filtration system 102 according to certain embodiments, with solid arrows indicating an example flow path for fluids and materials, and dashed arrows indicating an example flow path for signals and information. FIG. 2C illustrates the intake 104, the retentate outlet 106, the permeate outlet 108, a pump 222, a sensor 224, a filter 226, a processing unit 228, and an interface 230.

The pump 222 may be any device for inducing fluid flow through one or more portions of the filtration system 102. In certain embodiments, the pump 222 may be a peristaltic pump, which may reduce the need for sterilization of complex pump components; however, other types of pumps maybe used. The operation of the pump 222 may be controlled by modifying the operating parameters of the pump 222. This may enable the flow rate, pressure, and/or other parameters of the pump 222 to be changed. The pump 222 may also be used to withdraw the fluid from the reservoir 112.

The sensor 224 may be a device for generating and/or receiving information, including but not limited to one or more of characteristics of the fluid withdrawn from the reservoir 112, before, after, and/or during filtration, including but not limited to temperature; pressure; the ratio of permeate volume to retentate volume; the fluid flow rate to and/or from the reservoir 112; the amount of contaminants or other materials in the fluid; the fluid flow return rate; the filter efficiency; filter status (for example, whether the filters are clogged or otherwise running inefficiently); and other parameters or characteristics. While the sensor 224 is shown within the filtration system 102, one or more sensors 224 may be located elsewhere in the system 100 and/or cooperate with other locations. The sensor 224 may convert the data into computer- and/or human-readable representations for processing.

The filter 226 may be a device for separating a first portion of materials and/or fluid from a second portion of materials and/or fluid. The design and type of the filter 226 may vary depending on the type of fluid and the desired filtration results. For example, the filter 226 may be a tangential flow filter configured to separate the fluid into permeate and retentate (see, for example, FIG. 2D) with the retentate flowing to the retentate outlet 106 and the permeate flowing to the permeate outlet 108. For example, various combinations of filters may be used to achieve different kinds of filtration. For example, the filters may include filters of various pore sizes and different attributes. For example, filtering schemes may include ultrafiltration, microfiltration, macrofiltration and other sized filters that have various porosities. Combinations of filters may include dead end filtration, depth filtration, tangential flow filtration, affinity filtration, centrifugal filtration, vacuum filtration, and/or combinations thereof. Multiple filtration systems may be useful in order to continually re-filter retentate in order to yield a higher volume of permeate that may be returned to the reservoir 112.

The processing unit 228 may be a device configured to control the operation of the filtration system 102, for example by sending signals to the pump 222, sensor 224, and/or filter 226. In some embodiments, the signals are sent in response to receiving input from the interface 210. In certain embodiments, the processing unit 228 may be processing information, such as data received from the sensor 224 and/or the interface 210 and making decisions based on the information. In certain embodiments, the processing unit 228 may itself make decisions based on the information. For example, the processing unit 228 may include a processor and memory for running instructions configured to receive input, make decisions, and provide output.

The interface 230 may be a device or system of devices configured to receive input and/or provide output. In certain embodiments, the interface 230 is a keyboard, touchpad, subject monitoring device, and/or other device configured to receive input. For example, a healthcare professional may use the interface 230 to start or stop the system 100 and to modify system parameters, such as the absolute duration of the procedure, pump speed, and other parameters. The interface 230 may also include a display, speaker, or other device for sending user-detectable signals. In certain implementations, the interface 230 may comprise a network interface configured to send communications to other devices. For example, the interface 230 may enable the filtration system 102 to communicate with other filtration systems, flow control devices, a server, and/or other devices.

Figure 2D:
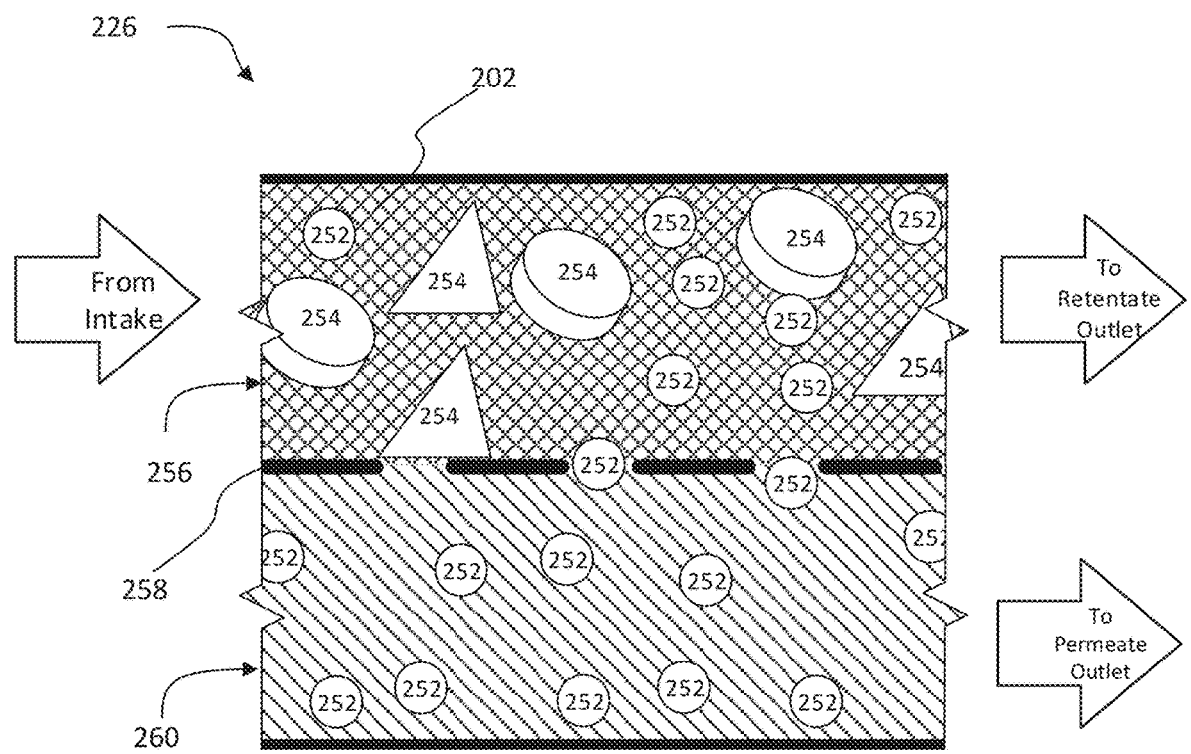
FIG. 2D illustrates a section of a tangential flow filtration system according to certain implementations.

FIG. 2D illustrates a segment of the filter 226 according to certain implementations, including a first section 256, a membrane 258, and a second section 260, with arrows indicating flow direction. As shown in FIG. 2D, the filter 226 is configured as a tangential flow filter. In this configuration, the fluid 202 may enter the filter 206 and pass through the first section 256. While the fluid 262 travels through the first section 256, the fluid 262 may encounter the membrane 258. A particular pressure, flow rate, or other environmental condition within the first section 256 and/or second section 260 may draw or otherwise encourage fluid to contact the membrane 258. The environmental condition may be created by, for example, the shape, size, or configuration of the filter 226. The environment may also be created as a result of the pump 222 or other feature of the filtration system 102 or system 100. As a result, certain components of the fluid 262 (for example, components 252) may pass through an aperture of the membrane 258 to the second section 260. However, certain other components (for example, contaminants 254) may be improperly sized (for example, the certain other components are too large) to pass through the membrane 258 and instead remain within the first section 256. The fluid 262 that passes through the membrane 258 into the second section 260 may be described as the permeate and may pass through to the permeate outlet 108.

As a specific example, the fluid 262 may be CSF having particular desirable components 252. The CSF may also contain contaminants 254, such as blood cells, blood cell fragments, hemolysis components, neutrophils, eosinophils, inflammatory cells, proteins, misfolded proteins, cytokines, bacteria, fungi, viruses, small and large molecules, oligomers (such as Aβ oligomers, tau oligomers, α-synuclein oligomers, and Huntingtin oligomers), antibodies (such as anti-myelin antibodies), enzymes, mutated enzymes (such as mutations to SOD1), and/or other substances. The contaminants 254 may, but need not, include materials or matter that are present in CSF normally (e.g. a cytokine that is present in CSF normally but is present in an elevated or otherwise undesirable amount). One or more of the contaminants 254 may be associated with or suspected to be associated with one or more diseases or conditions. For example, the contaminants 254 may be associated with one or more of Alzheimer's disease, Parkinson's disease, multiple sclerosis, Huntington's disease, amyotrophic lateral sclerosis, for instance, as described in U.S. application Ser. No. 13/801,215, previously incorporated by reference. The filter 226 may be used to separate the contaminants 254 from the fluid and/or desirable components 252 of the CSF. For instance, a membrane 258 may be sized or otherwise configured to allow CSF to flow through the membrane 258 while substantially preventing contaminants 254 from passing through the membrane 258.

Figure 3:
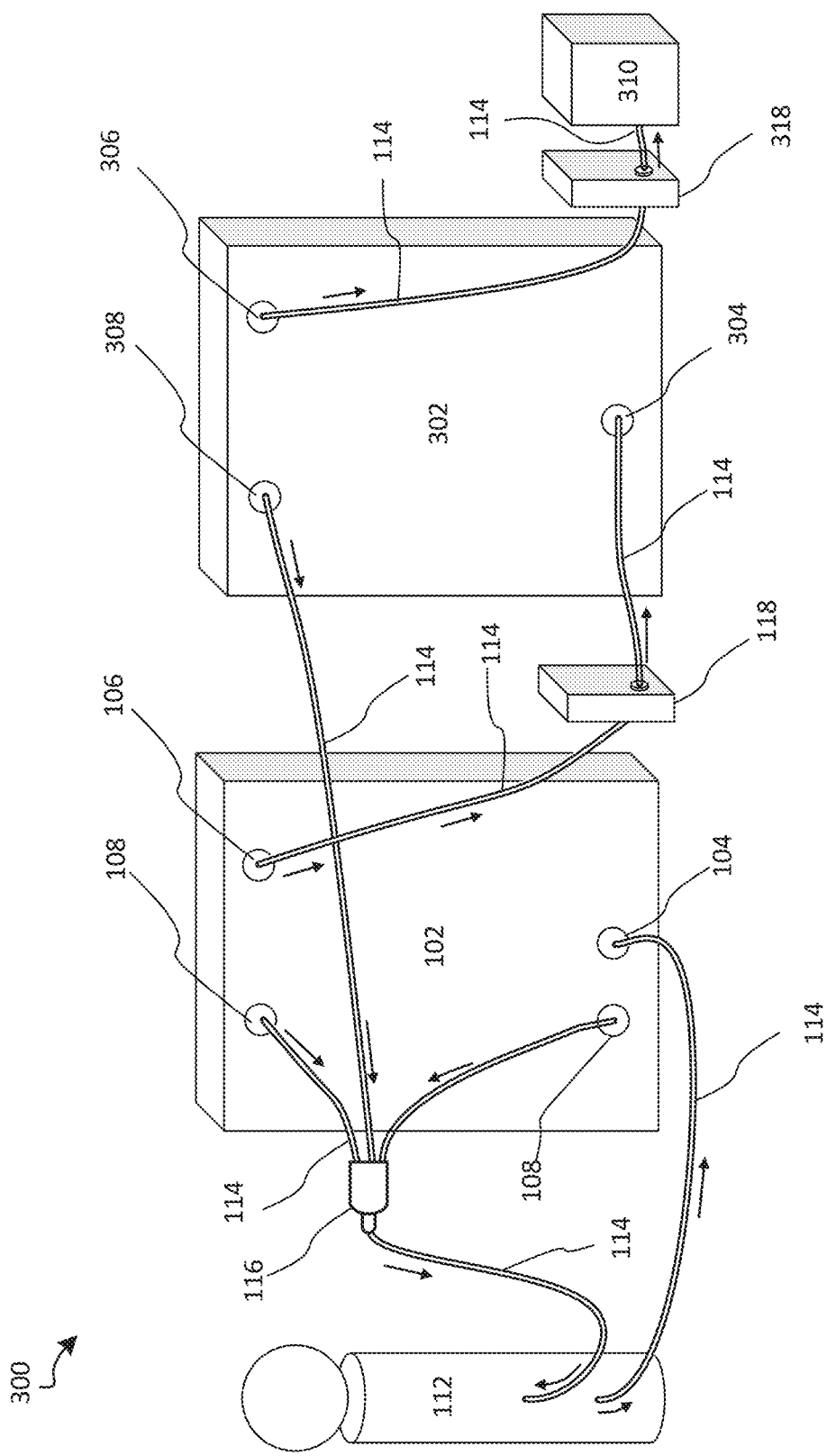
FIG. 3 illustrates a system for the filtration of materials from biologic fluids according to certain implementations, with solid arrows indicating an example fluid flow direction.

FIG. 3 illustrates a system 300 for the filtration of materials from biologic fluids according to certain embodiments. The system 300 may include additional components, such as but not limited to one or more flow (or pressure) regulators 118, 318, combiner 116, and filtration system 302 (for example, as described in reference to filtration system 102). Filtration system 302 may include an intake 304 (for example, as described above in reference to intake 104), a retentate outlet 306 (for example, as described in reference to retentate outlet 106), and a permeate outlet 308 (for example, as described above in reference to permeate outlet 108). The arrows represent flow direction.

In certain implementations, system 300 includes the filtration system 102 and, rather than having the retentate outlet 106 connected directly to the vessel 310, the retentate outlet 106 may be connected first to a flow regulator 118 and then to the intake 304 of the second filtration system 302. The permeate outlet 108 and permeate outlet 308 may be connected via a combiner 116 for flow to the reservoir 112. However, the permeate outlets 108, 308 need not necessarily be combined and may return via separate pathways to the reservoir 112. The retentate outlet 306 may be connected to the vessel 310 via a flow regulator 318.

The flow regulators 118, 318 may be devices configured to regulate one or more fluid flow characteristics of the system 300. These characteristics may include but are not limited to flow rate, direction, and pressure. While the flow regulators 118, 318 are illustrated as components outside of the filtration systems 102, 302, they need not be or need only be located outside of the filtration systems 102, 302 or in the exact locations illustrated. In certain embodiments, the flow regulators 118, 318 may be located within the filtration systems 102, 302. In certain implementations, the filtration systems 102, 302 or other portions of the systems 100, 300 may include additional flow regulators. The flow regulator may include various components or subsystems for controlling flow characteristics and may include pressure regulators, backpressure regulators, sensors, and/or other devices.

The flow regulators may be controllable by other components of the system (e.g., processing unit 228).

The combiner 116 may be a device in which the fluid from two or more tubes 112 is combined into a single fluid flow. For example, as illustrated in FIG. 3, the combiner 116 takes in fluid from the permeate outlet 108 and the permeate outlet 308 and combines the fluid into a single length of tubing 114 for deposit within the reservoir 112. In some embodiments, the combiner 116 may be a simple junction that places the flow from the outlets 108, 308 in fluid connection with the tubing 114 leading to the reservoir 112. In some embodiments, the combiner 116 may facilitate the mixing of the fluid. In certain embodiments, the combiner 116 may also include a mechanism for flow regulation. For example, the combiner 116 may smooth turbulent flow, buffer fluid for smooth deposit within the reservoir 112, remove air bubbles from the fluid, and perform other flow regulation or fluid treatment. The combiner 116 may also regulate the flow, direction, and pressure rate of the fluid being deposited within the reservoir 112.

The filtration system 302 may be a filtration system as described above in reference to filtration system 102. However, the filtration systems 102, 302 may be different. For example, the filtration system 102 may be configured to filter a particular kind of contaminant 254 while the filtration system 302 may be configured to filter a different kind of contaminant 254. In other embodiments, the filters may provide selective or progressive filtration, such as by having one set of pore sizes in filtration system 102 and then a set of smaller pore sizes in filtration system 302, such as to provide increased filtration of the same or different contaminants 254 and/or other substance or materials. One or both filtration systems 102, 302 may use tangential flow filtration, other filtration, or combinations thereof.

Figure 4:
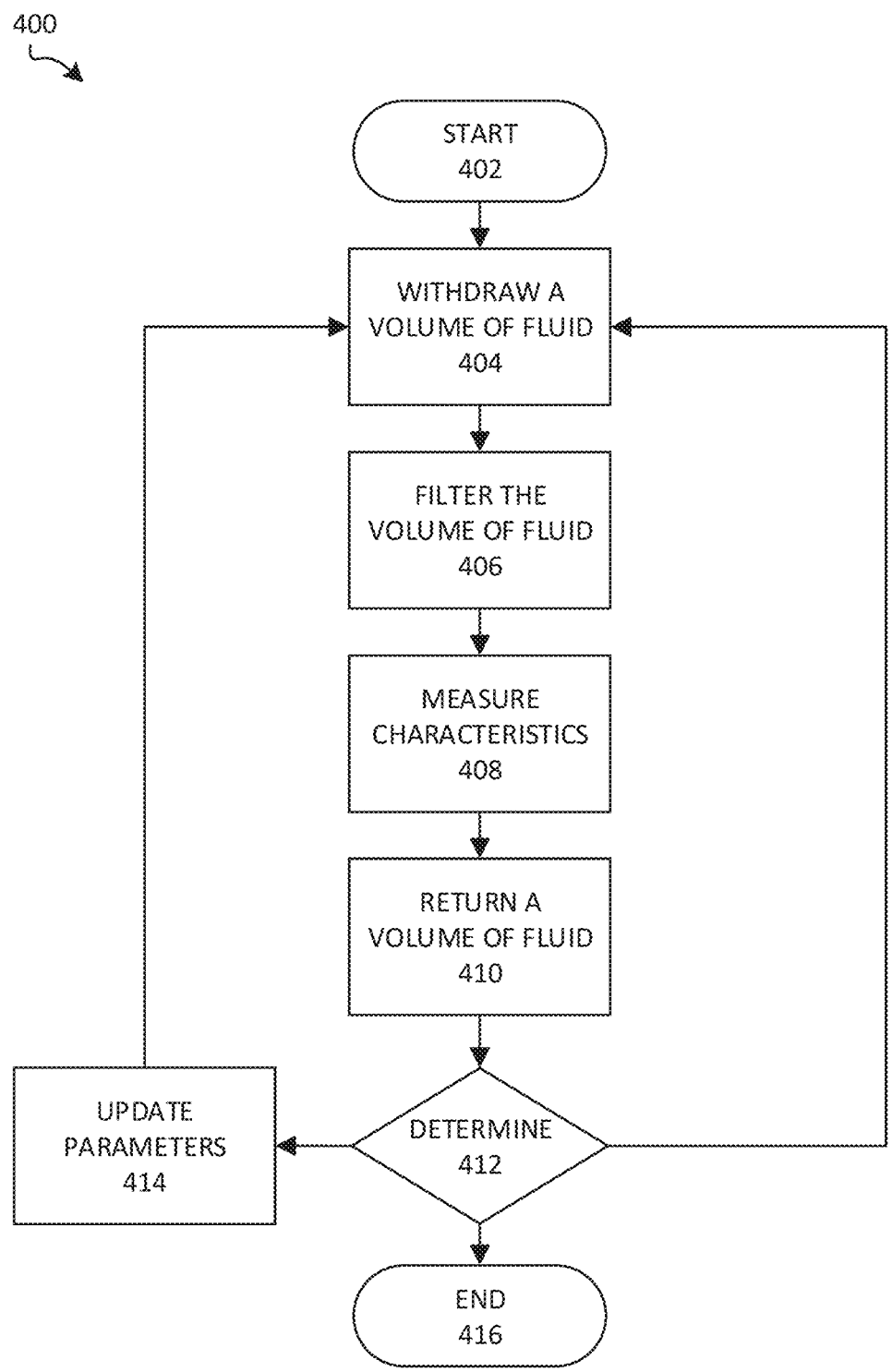
FIG. 4 illustrates a flow diagram for a method for using a filtration system for the filtration of materials from biologic fluids.

FIG. 4 illustrates a method 400 for using a filtration system for the filtration of materials from biologic fluids, including the steps of starting the process 402, withdrawing a volume of fluid 404, filtering and/or otherwise treating the volume of fluid 406, measuring characteristics 408, returning a volume of fluid 410, determining 412, updating parameters 414, and ending the process 416. The method may be utilized with certain embodiments, including system 100 and system 300. While the method will be described with reference to system 300, a person of skill in the art would be able to modify the steps in order to be used with other systems, including but not limited to system 100 or various combinations of systems.

While the method is described as being performed on a particular volume of fluid, the system may operate on a continuous flow of fluid. That is, the system 300 need not necessarily withdraw a volume of fluid, wait for the volume to be processed and returned, and then withdraw another volume of fluid. The method may follow a continuous process. Similarly, while FIG. 4 appears to illustrate a series of consecutive steps, the steps of the described method may occur concurrently. For example, the system 300 may concurrently perform some or all of the steps illustrated in FIG. 4. For instance, the system 300 may concurrently withdraw and return fluid.

The method 400 may begin at start 402. This step 402 may include activating one or more components of the system 300. This step 402 may also include or follow various preparation steps. Such steps may include installing filtration components, selecting and preparing the reservoir 112, installing tubing 114, calibrating components, priming components of the system 300, and other steps.

The installing filtration components step may include selecting particular filtration components based on desired outcomes, the particular reservoir 112, fluid, or other considerations. For example, if the method 400 is being used on a subject suffering from a cerebral vasospasm, the goal of the procedure may be to filter blood breakdown products from the subject's CSF. This would make the reservoir 112 a lumen carrying CSF, the fluid. As such, particular filtration components would be selected to filter the blood components from the CSF. For example, a membrane 258 with apertures sized to substantially prevent the flow of blood components, while large enough to substantially allow the entry of CSF as permeate, may be used.

The selecting and preparing the reservoir 112 step may include choosing a particular reservoir 112. For example, a healthcare professional may select an individual who may benefit from having filtration performed on a bodily fluid and identify a reservoir containing the fluid. This may include, as described above, a subject suffering from a cerebral vasospasm. Preparing the reservoir 112 may include identifying an anatomical location for a procedure to access the reservoir 112 (for example, in a spinal portion 200, as shown in FIG. 2A), sterilizing the location, or otherwise preparing the reservoir 112 for the procedure. Selecting and preparing the reservoir 112 may be performed according to the systems and methods described within this application or through other means. For example, selecting and preparing the reservoir 112 may be performed according to the various systems and methods described in U.S. patent application Ser. No. 14/743,652, previously incorporated by reference.

Installing tubing 114 may include connecting various components of the system 300. For example, retentate outlet 106 may be connected to flow regulator 118, flow regulator 118 to intake 304, and so on. This step may also include installing tubing 114 to withdraw fluid from and return fluid to the reservoir 112. This step may include inserting a multi-lumen catheter into an anatomical location to place the reservoir 112 in fluid connection with the system 300 to enable fluid to be drawn into the intake 104 and returned to the reservoir 112.

Calibrating components may include setting initial parameters for the use of the system 300. This step may include establishing an initial flow rate, an initial pressure, and other initial parameters or system settings. The initial parameters may be based on observed or predicted clinical measures, including but not limited to an estimated amount of fluid in the reservoir 112, the health of the subject, the predicted ratio of retentate to permeate, and other factors.

Priming the system 300 may include adding a priming solution to one or more of the components of the system 300. Depending on the configuration of the system 300, priming may be necessary for one or more components to function effectively. Depending on the reservoir 112, fluid, and the subject, priming may be necessary to assure comfort or good health. In certain applications, the system 300 may be primed to enable the return of a volume of fluid while simultaneously withdrawing a volume of fluid. This may be especially useful for applications where the reservoir 112 has a relatively small volume of fluid (e.g., during filtration of CSF) or is otherwise sensitive to relative changes in volume. Depending on the type of filtration being used, the length of the procedure, and other factors, priming fluid may be added during the filtration procedure to make up for fluid lost during the procedure At step 404, a volume of fluid is withdrawn from the reservoir 112. In certain circumstances, the fluid may be withdrawn using a pump or device located within the system 100. For example, the pump may be a component of one or more of the flow regulators 118, 318; the filtration systems 102, 302 (such as pump 222); and/or the combiner 116. The pump may be used to withdraw a volume of fluid from the reservoir 112.

In some embodiments, the rate at which the fluid is withdrawn from the reservoir 112 is between approximately 0.01 mL/min and approximately 100 mL/min. In preferable embodiments, the fluid rate may be 0.1 mL/min to approximately 10 mL/min. However, the amount withdrawn may be higher or lower depending on the application. The amount may vary depending on various factors including but not to the type of fluid being withdrawn, the viscosity of the fluid, the amount of fluid in the reservoir 112, and other factors. The viscosity of the fluid may vary over time, and depending on the particular subject. For example, the viscosity of CSF may be different in a subject with meningitis than a subject with typical CSF. Once the fluid is withdrawn from the reservoir 112, the fluid may pass through the tubing 114 and into the filtration system 102 via intake 104.

At step 406, the volume of fluid is filtered. This may include the steps of passing the fluid through a filter of the filtration system 102. While tangential flow filters have been described in this disclosure, they need not be the filter used, or need not be the only filter used. For example, the filtration system 102 may include various filtration component configurations including but not limited to tangential flow filtration, microfiltration, ultrafiltration, nanofiltration, dead-end filters, depth filters, and other filtration devices or mechanisms.

The filtration process may result in the separation of the fluid into a retentate flow and a permeate flow. The permeate flow may leave the filtration system 102 through a permeate outlet 108 and the retentate may leave the filtration system 102 through a retentate outlet 106. Depending on the configuration of the filters and the goals of the method 400, in some implementations, the permeate may be the fluid to be returned to the reservoir 112. In other implementations, the retentate may be returned to the reservoir 112. The retentate may be a fluid that contains contaminants or is otherwise in a condition undesirable for returning to the reservoir 112.

In certain embodiments, for example, as shown in FIG. 3, the retentate may be successively or progressively treated, such as by being filtered again through another filter process or by being filtered again through the same filter by being redirected through it. For example, in certain implementations, the retentate may be passed through a flow regulator 118 and into filtration system 302 for additional filtration. This filtration may result in the retentate being further separated into a second retentate and a second permeate. The second permeate may flow from the permeate outlet 308 to combiner 116 for return to the reservoir 112. The second retentate may be further filtered or purified. Once the fluid is sufficiently filtered, the remaining retentate or contaminants may be passed through a flow regulator 318 and into a vessel 310 for analysis, disposal, storage, or other use, or, alternatively, or in addition, the remaining retentate may be subjected to further processing, treatment, and/or filtration (any number of times), where the further treated fluid is, for example, directed to reservoir 112, either directly or in combination with other fluids.

At step 408, characteristics of the fluid and/or the system may be measured. Measuring characteristics may include intermittent or continuous sampling and/or monitoring of characteristics or parameters of interest. While this step 408 is shown as occurring after the filtration of the fluid 406, the step 408 may take place at any point during the process 400 where useful data may be gathered.

In certain embodiments, measuring characteristics may include measuring the characteristics of the fluid withdrawn from the reservoir 112 before, during, or after filtration. The characteristics measured may include the presence or amount of particular contaminants, proteins, compounds, markers, and other fluid components present. As another example, the ratio of permeate volume to retentate volume, the fluid flow rate from the reservoir 112, fluid temperature, fluid opacity or translucency or transparency, an absolute retentate flow rate, and the rate of fluid flow to the reservoir 112 also may be measured. The performance characteristics of the system 300 may also be measured. For example, the efficiency of the filter 226, the status of the filter 226 (for example, via the interface 210), and other markers of system 300 performance.

In certain embodiments, the characteristics measured may include information about a subject or input by a healthcare provider. For example, the system 300 may monitor the blood pressure, heart rate, stress, and other information of the subject. In addition to quantitative characteristics, qualitative measurements may be made as well. For instance, subject discomfort and other qualities may be measured. These and other data may be measured by the sensor 224 and/or be input into the system by an input device (for example, keyboard, touch screen, subject-monitoring device, and other devices for receiving input) operably coupled to the system 300.

At step 410, a volume of fluid is returned to the reservoir 112. In certain embodiments, the fluid is returned to the reservoir 112 as soon as fluid filtration has been completed. In certain embodiments, the flow rate of the fluid may be controlled. For example, a volume of fluid may be buffered at the combiner 116 or in another area of the system 300 for a time before being returned to the reservoir 112. Buffering may be used to smooth the return rate of the fluid, to allow time for the fluid to reach a particular temperature, to allow time for a particular additive to mix within the fluid, and for other reasons.

In certain embodiments, the rate and/or pressure at which the fluid is returned to the reservoir 112 is controlled (for example, by the combiner 116 and/or the flow regulator 318). For example, the return of fluid is controlled so that the fluid is returned at such a rate or in such a manner as to maintain homeostasis within the reservoir 112. In certain embodiments, this may be accomplished by returning fluid at the same rate at which fluid is currently being withdrawn from the system. In certain embodiments, the fluid may be returned at substantially the same flow rate at which it was removed. The fluid volume removed from the system and returned to the system may not be equal. This may be the case when removing a significant quantity of contaminants from a reservoir. In certain embodiments, the difference may be made up through the addition of additional fluid.

In certain embodiments, a particular volume of additional fluid may be returned to the reservoir 112. The additional fluid may be fluid that was not withdrawn from the reservoir 112, previously withdrawn from the reservoir 112, withdrawn from a different reservoir, synthetically created, or is otherwise different from the volume removed from the reservoir 112 in step 404. The return of additional fluid may be used to, for example, compensate for the volume of fluid that was filtered out, especially in circumstances where the reservoir 112 comprised only a small amount of fluid at the start 402.

In certain embodiments, one or more therapeutic agents may be added to the fluid prior to its return to the reservoir 112. The fluid may be treated or mixed with a particular pharmacological agent. For example, when the fluid is CSF, the agent may be configured to bypass the blood-brain barrier. The agents may include, but need not be limited to, antibiotics, nerve growth factor, anti-inflammatory agents, pain-relief agents, agents designed to be delivered using intrathecal means, agents designed to affect a particular condition (e.g., meningitis, Alzheimer's disease, depression, chronic pain, and other conditions), and other agents.

As a specific example, the reservoir 112 may be a CSF-containing space of a subject, such as the subarachnoid space or another space known or thought to contain CSF. The space may only have a total of approximately 125 ml of CSF, and if the level drops below a certain threshold (for example, approximately 85 ml), the subject may suffer undesirable side effects. If a particularly large amount of the existing CSF comprises undesirable compounds, the volume of permeate may be small enough to cause the fluid levels in the reservoir 112 to drop below the threshold. Consequently, the system 300 may return a volume of additional fluid (for example, artificial CSF or other suitable fluid) to adjust for the difference between the amount of withdrawn CSF being returned and the amount needed to be returned in order to maintain the volume of the reservoir 112 above the threshold amount.

In certain embodiments, the withdrawal and return of the fluid may occur in a pulsed manner. For example, the system 300 may withdraw a particular volume and then cease withdrawing additional fluid. The withdrawn volume is processed by the filtration or other systems and be buffered (for example, at the combiner 116). Filtered amount from the buffer may be returned to the reservoir 112 at about the same rate and/or for the about same total volume as a next volume is withdrawn from the reservoir 112. This process may allow the system to maintain reservoir 112 volume levels relatively consistent and may be useful in circumstances where the processing time (for example, the time between the fluid being withdrawn from and returned to the reservoir 112) is long.

At step 412, a determination is made. The determination may be made by, for example, a healthcare professional, a processor system, or a combination thereof. For example, the healthcare professional may analyze the measure characteristics and come to a conclusion. As another example, the processing unit 208 may analyze the measured characteristics based using an algorithm or through other mechanisms. The determination may be based on the measured parameters, a timer, a schedule, or other mechanisms. The determination may be used in order to change the parameters of the system 300 to change over time and to address particular measured characteristics.

For example, a determination may be made regarding the flow rate at which the fluid is being withdrawn and/or returned to the reservoir 112. For example, it may be desirable to maintain substantially the same withdrawal and return rate of the fluid. Specifically, if more fluid is being withdrawn from the reservoir 112 than is being returned, then the volume of fluid in the reservoir 112 may be decreasing overall. This may be undesirable because for certain fluids and certain reservoirs 112, if the volume of the reservoir 112 passes a particular threshold, undesirable side effects may occur. For instance, where the fluid being withdrawn is CSF, the flow rate may be such that the volume of CSF removed from a human subject does not exceed about between approximately 5 mL and approximately 20 mL over the course of one hour. That is, the volume of fluid does not decrease more than approximately 5 mL to approximately 20 mL from its original starting volume in a one hour period of time. In certain embodiments, it may be desirable to maintain an absolute retentate flow rate within a certain range of acceptable retentate flow rates. In certain embodiments, the threshold may be between approximately 0.10 mL/min and approximately 0.30 mL/min. In certain embodiments, the threshold may be approximately 0.16 mL/min. In certain embodiments, the threshold may be between approximately 0.2 mL/min and approximately 0.25 mL/min; however, other values may be desirable in certain circumstances. In certain embodiments, a pump may be running at approximately 1.0 mL/min and the retentate flow rate is approximately 0.25 mL/min, the permeate flow rate is approximately 0.75 mL/min, which is about a 3:1 ratio. However, if the pump speed were increased to approximately 2.0 mL/min, the retentate flow rate may be held at approximately 0.25 mL/min, which leaves the permeate flow rate as approximately 1.75 mL/min, or about a 7:1 ratio. By maintaining the retentate flow rate within the threshold, the system may be considering functioning as intended, despite the change in ratios.

Based on the measured characteristics, it may be determined that the best way to address the disparity in the withdrawal and return rates may be to decrease the flow rate to reduce the overall volume of fluid lost from the system. This may mean that, although there is a net loss of fluid from the reservoir 112, the loss is occurring at a slower rate. The rate may be sufficiently slow that, for example, that the subject's body produces sufficient fluid to make up for the loss.

For example, at the beginning of the filtration process 400, the fluid may contain large amounts of contaminants, resulting in a comparatively large amount of material being filtered out and a comparatively small amount of the fluid being returned (for example, permeate). As the filtration or treatment process continues, the amount of fluid being treated may decrease because the contaminants have already been filtered out (for example, retentate). In this scenario, a determination may be made to begin the process at a relatively low flow rate and then increase it as the volume of the fluid being filtered out decreases. In addition, the determination may include altering the flow and/or pressure within the filter 226 in order to achieve particular filtering results.

As another example, the measured characteristics may be a subject's expressed discomfort. Withdrawing CSF from a CSF-containing space of a subject may cause symptoms of overdrainage, such as spinal headache. Symptoms of overdrainage may be able to be avoided or otherwise addressed by not withdrawing more than a threshold amount of CSF. However, the particular threshold may vary from subject to subject. As such, a predicted threshold may be different from an actual threshold and the subject may experience symptoms sooner than expected. In response to the subject expressing feelings of discomfort, the healthcare professional may determine that the parameters of the process may need to be changed.

In certain embodiments, at step 412, the processing unit 228 and/or a healthcare professional may determine that the process should be completed. At this point, the flow diagram moves to end step 416. In certain other embodiments, at step 412, the processing unit 228 and/or a healthcare professional may determine that the process should continue substantially unchanged. Upon that determination, the flow diagram may return to step 404. In still other embodiments, at step 412, the processing unit 228 and/or a healthcare professional may determine that the one or more parameters of the process should be changed. Upon that determination, the flow diagram may move to step 414.

At step 414, one or more parameters of the system 300 are changed in response to a determination made in step 412. The parameters to be changed may include inflow rate, outflow rate, buffer size, and other parameters. Such parameters may be changed via, for example, the processing unit 206 sending a signal to the pump 222 or other component of the system in order to modify the parameters. In certain embodiments, the parameters may be manually changed through input received at the input 208. This may include parameters entered by a healthcare professional. In certain embodiments, parameters may be updated based on the difference between the withdrawal volume and the returned volume (e.g., a waste rate).

In certain embodiments, the updating parameters step 414 may include changing the flow direction of the fluid. For example, a system may include a plurality of filtration systems, which the fluid may be directed to by the manipulation of a valve or other mechanisms for changing fluid flow direction. Step 414 may include changing the fluid flow from one filtration system to a different filtration. This may be in response to determining that a second filtration system (for example, filtration system 302) is more suited for filtering particular contaminants than a first filtration system (for example, filtration system 102).

In certain embodiments, the updating parameters step 414 may include modifying the positioning of the tubing at the reservoir 112. For example, one or more inflow or outflow tubes 114 may become clogged or otherwise be operating at a reduced capacity. In response, the tubing 114 may be adjusted or otherwise modified to address the reduced capacity issue. The healthcare professional may be alerted to the issue by a light, alarm or other indicia.

In certain embodiments, the updating parameters step 414 may include cleaning or otherwise modifying one or more components of the system 300, such as the filter 226. This may be accomplished by, for example, changing back pressure and pump speed.

In certain embodiments, the updating parameters step 414 may include sensing characteristics of the system to determine whether the filter 226 or other components of the system are experiencing clogging. The sensed characteristic may include reading an alert state of the filtration system or detecting an increase in filter pressure with no change to system flow rates or other parameters of the system. Responsive to determining that there may be a clog in the system 300, the flow rate through the retentate port of the filters may be increased. The increased flow rate may be the result of a user or the system opening a back pressure valve (e.g., a backpressure valve of the flow regulators 118, 318). The opening of the valve may result in a surge of fluid through one or more retentate ports of one or more filters into a waste collection area (e.g., vessels 110, 310). The surge of fluid may result in the flow returning to the reservoir 112 reducing to zero or even a negative rate. Thus, the operator or system controlling the flow rate may take into account the volume of fluid lost and the possible effects on the patient as a result of this filter clearance mechanism.

Figure 5:
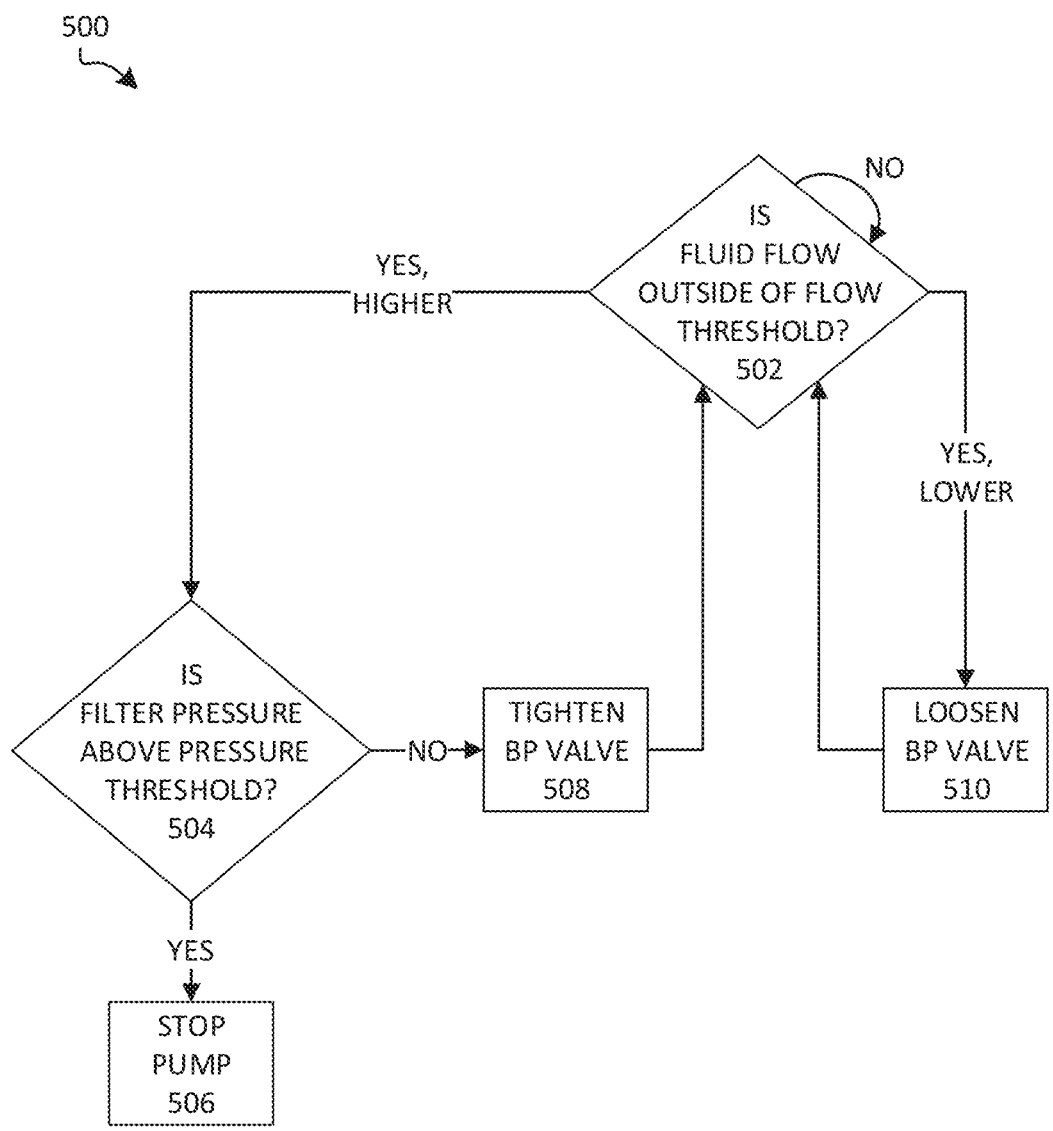
FIG. 5 illustrates a flow diagram for a method of controlling fluid flow within a filtration system.

In certain embodiments, the updating parameters step 414 may include operating a fluid flow control method, such as a method 500 as shown in FIG. 5. The method 500 may be used, in part, to control the flow of fluid through the system, such as the flow of retentate, permeate, waste, and/or other fluids. The fluid flow control method may include the steps of determining if the fluid flow is outside of a flow threshold 502, determining if the flow pressure is above a pressure threshold 504, stopping the pump 506, tightening a backpressure valve 508, and loosening a backpressure valve 510 (e.g., a backpressure valve of the flow regulator 118, 318 or elsewhere within a system). While fluid is flowing through the system (e.g. system 100, 300), a sensor of the system may detect a fluid flow rate (e.g., the rate at which fluid is traveling to waste, such as to vessel 110, 310) and compare it to a threshold. If the fluid flow rate is at a threshold or within a threshold range, then no substantial changes may be needed. If the fluid flow rate is above the threshold range, then the method may proceed to step 504. If the fluid flow is below the threshold range, then the method may proceed to step 510. The sensing of the flow rate may be continuous or occur periodically. In certain implementations, proceeding to the step 504, 510 need not occur immediately upon detecting a flow outside of the flow threshold; instead, the method may proceed to the step 504, 510 after the flow is outside of the flow threshold for a particular number of checks (e.g., two or more checks of the waste flow rate). In certain embodiments, the threshold range for the fluid flow rate may be between approximately 0.2 mL/min and approximately 0.25 mL/min; however, other values may be used depending on particular implementations.

Step 504 may be reached when the fluid flow is higher than the threshold flow range. At this step, it is determined whether a pressure at or of the filter is above a pressure threshold. If the pressure is above the pressure threshold, then the method moves to step 506 and the pump is stopped. If the pressure is not above the threshold, then the method moves to step 508 where a backpressure valve is tightened and the method then returns to step 502. In certain embodiments, the threshold pressure may be 1,100 mmHg; however, other thresholds may be appropriate. Step 510 may be reached if the flow rate is lower than the flow threshold. In this step, the backflow pressure valve may be loosened and the method then returns to step 502.

Returning to FIG. 4, at step 416, the process comes to an end. After the process is completed, various wind-up steps may be performed, including but not limited to, applying a bandage to the subject, disassembling one or more components of the system 300, analyzing an amount of the withdrawn fluid, analyzing the retentate, and other steps.

Some therapies involve filtering bodily fluid to remove a waste product. In some such therapies, CSF is passed through a tangential flow filter system to filter waste from the CSF by separating the CSF into permeate and retentate. The waste fluid (typically the retentate) leaves the tangential flow filter system and is shunted to a waste bag. This waste fluid often still contains non-waste, desirable fluid (e.g., CSF) that can be returned to the subject. The removal of such non-waste fluid contributes to fluid loss and a waste rate of the system. The waste rate is the amount of product that the system removes from a subject that is not returned to the subject. For example, if a system removes 0.50 mL/min of CSF and returns 0.40 mL/min of CSF, then the waste rate is 0.10 mL/min of CSF.

Some therapies involving filtering low volumes of fluid can present special challenges. For example, human and animal subjects have a limited amount of CSF and withdrawing too large of a volume of CSF from a subject can cause symptoms of overdrainage, such as spinal headache. This can be managed by not withdrawing more than a particular volume of CSF at one time and by keeping the waste rate of the system low (e.g., lower than the subject's predicted natural CSF replenishment rate). However, some filtration systems, such as tangential flow filter systems, require a certain waste rate, overall flow rate, or total volume to function efficiently. These rates may be undesirably high and may cause side effects in the subject. Tangential flow filtration systems allow material too large to pass through the filter to roll across the filter and out a separate port, preventing the clogging. However, some of the desired fluid is also lost to this process as the waste and desired fluid are shunted away to a waste bag. If the flow rate (and therefore waste rate) is kept too low, then an insufficient rate or volume of flow across the filter membrane may result in clogging or reduced effectiveness of the filter. Other filtration systems (e.g., dead end filters or depth filters) may not have the high rate or volume requirements of a tangential flow filter system, but may clog easily, cause blood lysis, and/or cause pressure increases. Although filtering systems can be used to enhance certain aspects of fluid filtration, there is a need for improved designs. In particular, there remains a need for products and techniques that provide for a more robust approach to filtering fluid while minimizing overdraining and the limitations of individual filtration systems.

Relevant to overcoming such limitations are systems and methods involving performing a first filtration pass with one or more tangential flow filtration systems and then filtering the waste from the tangential flow filtration system through a dead end filter, depth filter, or other filter. In this manner, flow rate across the tangential flow filter membrane may be kept high while the flow rate going through the dead end depth or other filter would be low, thereby slowing any clogging. The dead end or depth filter may act in place of a waste bag, slowly collecting the waste product while allowing the desired fluid to pass through and be returned to the subject. By replacing the waste bag with a dead end or depth filter, this desirable fluid can be separated from waste materials and returned to the subject, thus reducing the waste rate. In this manner, the system supports the advantages of both filtering methods individually while ameliorating their individual drawbacks.

Figure 6:
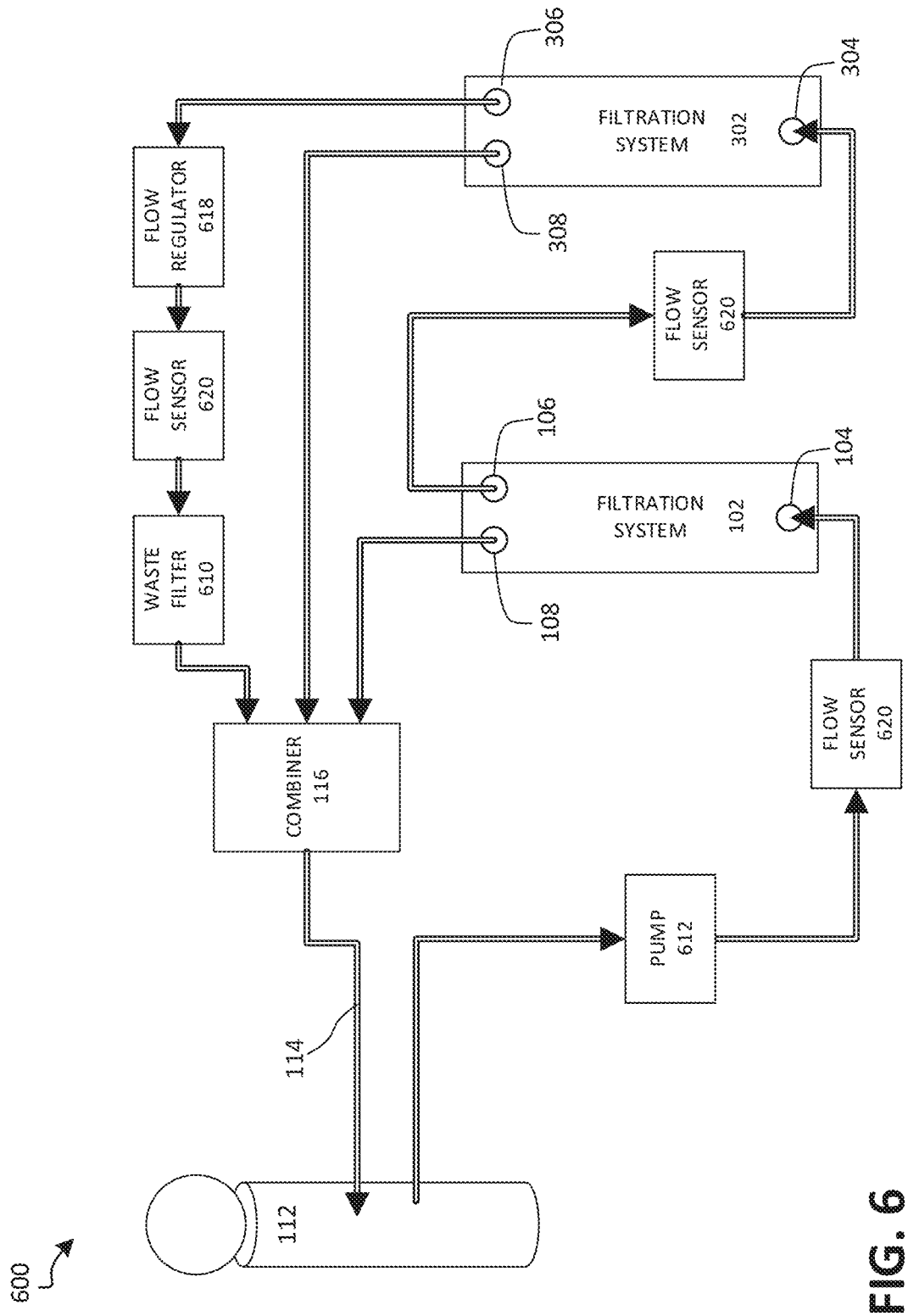
FIG. 6 illustrates a system for the filtration of materials from biologic fluids according to certain implementations.

FIG. 6 illustrates a system 600 for the filtration of materials from biologic fluids according to certain implementations. The system 600 may include one or more components similar to those describe in relation to FIG. 1 and FIG. 3, such as filtration systems 102, 302; intakes 104, 304; retentate outlets 106, 306; permeate outlets 108, 308; reservoir 112; tubing 114; and combiner 116. The system 600 may further include one or more additional components, including a waste filter 610, a pump 612, a flow regulator 618, and a flow sensor 620.

The waste filter 610 may be a filter adapted to provide filtered fluid by removing waste or other substances from fluid flowing through the waste filter 610. The waste filter 610 may include one or more of a variety of different kinds of filters, including a dead end filter, depth filter, and other filters. The waste filter 610 may also incorporate a reservoir to capture additional waste volume relative to a standard dead end filter, depth filter, or other filter. The waste filter 610 may be adapted to remove one or more particular substances from particular fluids, such as blood from CSF. To prevent back flow into the waste filter 610, the combiner 116 may include a check-valve at the point the filtered waste is connected.

The pump 612 may be a pump used to withdraw fluid from the reservoir 112 and provide the fluid to other components of the system 600. The pump may include one or more characteristics of pump 222. The flow regulator 618 may include one or more characteristics of other flow regulators described herein, such as flow regulators 118, 318. The flow regulator may include a backpressure valve, such as a backpressure valve configured to prevent reverse flow. The flow sensors 620 may be one or more sensors configured to generate and/or receive information, including but not limited to one or more of characteristics of the fluid. The flow sensors 620 may have one or more characteristics in common with the sensor 224.

An example fluid flow path for system 600 begins at reservoir 112. The pump 612 draws fluid from the reservoir 112, and the fluid passes a flow sensor 620 towards the intake 104 of the filtration system 102. The filtration system 102 includes a tangential flow filter and separates the fluid into permeate and retentate. The retentate leaves the filtration system 102 via the retentate outlet 106, and the permeate leaves the filtration system 102 via the permeate outlet 108 and travels to the combiner 116. The retentate passes a flow sensor 620 and enters the intake 304 of the filtration system 302. The filtration system 302 includes a tangential flow filter and separates the fluid into permeate and retentate. The retentate leaves the filtration system 302 via the retentate outlet 306, and the permeate leaves the filtration system 302 via the permeate outlet 308 and travels to the combiner 116. From the retentate outlet 306, the retentate passes a flow regulator 618 and a flow sensor 620 and enters an intake of the waste filter 610. The flow sensor 620 may monitor the fullness or potential to clog for the waste filter 610. The waste filter 610 filters the retentate and the filtered retentate leaves an outlet of the waste filter 610 and enters the combiner 116. At the combiner 116, the fluid received at the combiner 116 from the filtration system 102, the filtration system 302, and the waste filter 610 is combined and returned to the reservoir 112.

During operation of the system 600, a waste rate of the filtration system may be calculated or measured, and one or more parameters of the system 600 may be modified to maintain a waste rate of less than a threshold. The parameters may include fluid flow rates, rate of addition of artificial CSF, filtration parameters, and other parameters. In some examples, the threshold is 0.20 mL/min of CSF. In some examples, the threshold may be a predicted rate of natural CSF production in the subject. In some human subjects a predicted rate of natural CSF production may be 0.25 mL/min.

Figure 7:
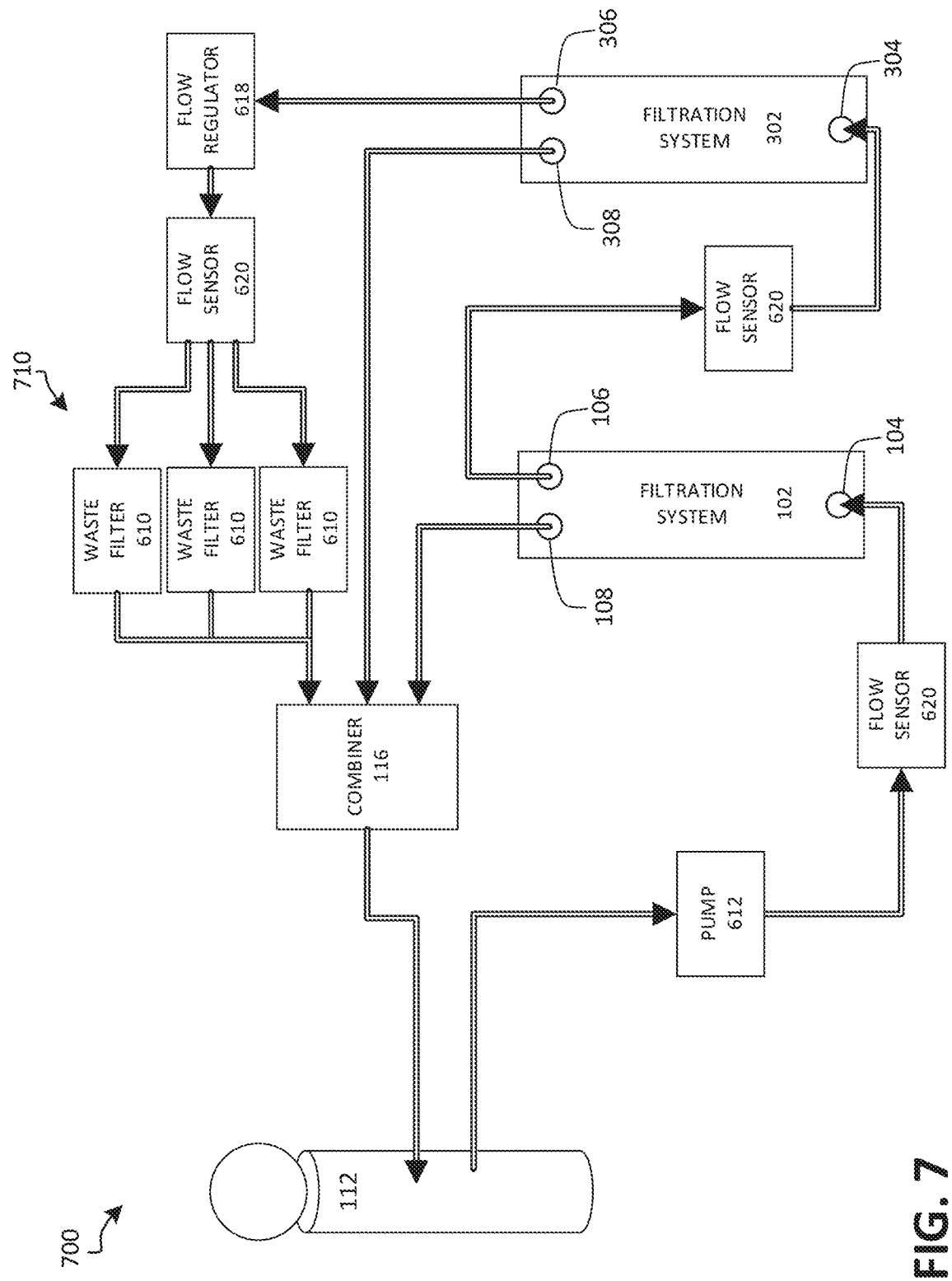
FIG. 7 illustrates a system for the filtration of materials from biologic fluids according to certain implementations.

FIG. 7 illustrates a system 700 for the filtration of materials from biologic fluids according to certain implementations. The system 700 may include one or more components similar to those described in relation to FIG. 1, FIG. 3, and FIG. 6. Compared to the example system 600 illustrated in FIG. 6, the example system 700 illustrated in FIG. 7 includes a plurality of waste filters 610 arranged in a filtration system 710.

The filtration system 710 includes a plurality of waste filters 610 for filtering fluid entering the filtration system 710. The filtration system 710 may operate in a variety of ways. In an example, fluid may be directed to a first subset of the plurality of filters 610 at one time, with the fluid being directed to a second subset of filters based on measured parameters of the filtration system 710 a later time. For instance, the fluid may be directed to the first subset of filters 610 until it is detected that the first subset of filters are full, clogged, less efficient, or otherwise determined to have reached an unsuitable threshold. At that time, a valve of the filtration system 710 may direct the fluid flow to the second subset of filters rather than the first subset. In an example, the filters 610 are placed in parallel. In this manner, the filtration system 710 may be a self-regulating system, such that as one or more waste filters became full or clogged, pressure increases and results in more waste fluid being directed to other waste filters of the plurality of parallel waste filters.

An example fluid flow path for system 700 may be similar to the example path described with regard to system 600. There may be one or more differences in the example fluid flow path for system 700 compared to system 600 regarding the waste filter 610. For example, in system 700, fluid may travel from the retentate outlet 306, pass a flow regulator 618 and a flow sensor 620 to the filtration system 710. The fluid entering the filtration 710 may be split among the plurality of waste filters 610 of the filtration system 710.

Within this disclosure, connection references (for example, attached, coupled, connected, and joined) may include intermediate members between a collection of components and relative movement between components. Such references do not necessarily infer that two components are directly connected and in fixed relation to each other. The exemplary drawings are for purposes of illustration only and the dimensions, positions, order and relative sizes reflected in the drawings attached hereto may vary.

The above specification provides a complete description of the structure and use of exemplary embodiments as claimed below. Although various embodiments of the invention as claimed have been described above with a certain degree of particularity, or with reference to one or more individual embodiments, those skilled in the art could make numerous alterations to the disclosed embodiments without departing from the spirit or scope of this disclosure. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the disclosure as defined in the following claims.

What is claimed is:

1. A system for filtering materials from cerebrospinal fluid (CSF) of a human or animal subject, the system comprising:
    a catheter assembly including a first fluid pathway and a second fluid pathway;
    a first tangential flow filter coupled to the catheter assembly, the first tangential flow filter having a fluid inlet in communication with the first fluid pathway, a permeate outlet in fluid communication with the second fluid pathway for a permeate flow, and a retentate outlet for a retentate flow;
    a second tangential flow filter having an intake and an outlet, the intake coupled to the retentate outlet of the first filter, and the outlet in fluid communication with the second fluid pathway of the catheter assembly;
    a pump configured to withdraw a volume of cerebrospinal fluid from the human or animal subject and transfer the volume of cerebrospinal fluid to the first tangential flow filter along the first fluid pathway;
    wherein the first and second tangential flow filters are is configured to filter the volume of cerebrospinal fluid into a permeate and a retentate;
    wherein the pump is configured to return at least a portion of the permeate to the human or animal subject along the second fluid pathway; and
    a processor configured for measuring a waste rate of the system, wherein the waste rate is the difference between the volume of fluid withdrawn from the subject and a volume of permeate returned to the subject over a period of time.

2. The system of claim 1, wherein the processor is configured for modifying one or more parameters of the system that influence the waste rate to maintain the waste rate less than a threshold waste rate.

3. The system of claim 2, wherein the one or more parameters of the system include one or more of: rate of withdrawal of cerebrospinal fluid from the subject; rate of return of permeate to the subject; and rate of addition of artificial cerebrospinal to the volume of permeate returned to the subject.

4. The system of claim 2, wherein the threshold waste rate is 0.25 milliliters per minute.

5. The system of claim 1, wherein the processor is configured to maintain the waste rate within a predetermined threshold range.

6. The system of claim 5, wherein the processor is configured such that when the measured waste rate is above the predetermined threshold range, the processor modifies one or more parameters of the system that influence the waste rate to bring the waste rate down into the predetermined threshold range.

7. The system of claim 6, wherein the processor is configured such that when the measured waste rate is below the predetermined threshold range, the processor modifies one or more parameters of the system that influence the waste rate to bring the waste rate up into the predetermined threshold range.

8. The system of claim 7, wherein the predetermined threshold range is between 0.2 milliliters per minute and 0.25 milliliters per minute.

9. The system of claim 1, wherein the catheter assembly includes a dual lumen catheter.

10. A system for filtering materials from cerebrospinal fluid (CSF) of a human or animal subject, the system comprising:
    a catheter assembly including a first fluid pathway and a second fluid pathway;
    a first tangential flow filter coupled to the catheter assembly, the first tangential flow filter having a fluid inlet in communication with the first fluid pathway, a permeate outlet in fluid communication with the second fluid pathway for a permeate flow, and a retentate outlet for a retentate flow;
    a second tangential flow filter having an intake and an outlet, the intake coupled to the retentate outlet of the first filter, and the outlet in fluid communication with the second fluid pathway of the catheter assembly;
    a pump configured to withdraw a volume of cerebrospinal fluid from the human or animal subject and transfer the volume of cerebrospinal fluid to the first tangential flow filter along the first fluid pathway;
    wherein the first and second tangential flow filters are configured to filter the volume of cerebrospinal fluid into a permeate and a retentate;
    wherein the pump is configured to return at least a portion of the permeate to the human or animal subject along the second fluid pathway; and
    one or more sensors for measuring a waste rate of the filtration system, wherein the waste rate is the difference between the volume of cerebrospinal fluid withdrawn from the subject through the first fluid pathway and a volume of permeate returned to the subject along the second fluid pathway.

11. The system of claim 10, further including an interface configured to receive input from a user for modifying one or more parameters of the system that influence the waste rate, for the user to maintain the waste rate less than a maximum threshold.

12. The system of claim 11, wherein the threshold is 0.25 milliliters of CSF per minute.

13. The system of claim 11, wherein the one or more parameters include flow rate, pressure, rate of addition of artificial CSF to the permeate returned to the subject, one or more filtration parameters, or combinations thereof.

14. The system of claim 10, further including a processor in communication with the one or more sensors, the processor being configured to calculate the waste rate and for modifying one or more parameters of the system that influence the waste rate to maintain the waste rate less than a threshold.

15. The system of claim 14, wherein the processor includes an interface configured to receive input from a user for modifying one or more parameters of the system that influence the waste rate for the user to maintain the waste rate less than a maximum threshold.

16. The system of claim 14, wherein the one or more parameters include flow rate, pressure, rate of addition of artificial CSF to the permeate which is returned to the subject, one or more filtration parameters, or combinations thereof.

17. The system of claim 14, wherein the threshold is 0.25 milliliters per minute.

18. A system for filtering materials from cerebrospinal fluid (CSF) of a human or animal subject, the system comprising:
- a catheter assembly including a first fluid pathway and a second fluid pathway;
- a first filter comprising a tangential flow filter configured to filter a volume of CSF into permeate and retentate, the first filter having a fluid inlet in communication with the first fluid pathway, a permeate outlet in fluid communication with the second fluid pathway for a permeate flow, and a retentate outlet for a retentate flow;
- a second filter having an intake and an outlet, the intake coupled to the retentate outlet of the first filter, and the outlet in fluid communication with the second fluid pathway of the catheter assembly; and
- a processing unit for calculating a waste rate of the system and modifying one or more parameters of the system that influence the waste rate to maintain the waste rate less than a preset threshold, wherein the waste rate is the difference between a volume of CSF removed from the subject through the first fluid pathway and a volume of CSF returned to the subject through the second fluid pathway.

19. The system of claim 18, wherein the threshold is 0.25 milliliters per minute.

* * * * *